United States Patent
Bartlett et al.

(10) Patent No.: US 11,786,613 B2
(45) Date of Patent: Oct. 17, 2023

(54) MAGNETIC TRACER COMPOSITIONS

(71) Applicant: Ferronova Pty Ltd, Adelaide (AU)

(72) Inventors: Stewart Gavin Bartlett, Goodwood (AU); Melanie Ruth Maria Nelson, Brompton (AU); Benjamin Thierry, Fitzroy (AU); Aidan Cousins, Ridgehaven (AU); Thi Hanh Nguyen Pham, Yagoona (AU); Brian Stanley Hawkett, Mona Vale (AU)

(73) Assignee: FERRONOVA PTY LTD, Adelaide (AU)

( * ) Notice: Subject to any disclaimer, the term of this patent is extended or adjusted under 35 U.S.C. 154(b) by 0 days.

(21) Appl. No.: 17/497,119

(22) Filed: Oct. 8, 2021

(65) Prior Publication Data

US 2022/0023446 A1    Jan. 27, 2022

Related U.S. Application Data

(63) Continuation of application No. PCT/AU2020/051264, filed on Nov. 20, 2020.

(30) Foreign Application Priority Data

Nov. 21, 2019  (AU) .............................. 2019904407

(51) Int. Cl.
A61K 49/18        (2006.01)

(52) U.S. Cl.
CPC ...... *A61K 49/1854* (2013.01); *A61K 49/1857* (2013.01)

(58) Field of Classification Search
CPC ........................ A61K 49/1854; A61K 49/1857
See application file for complete search history.

(56) References Cited

U.S. PATENT DOCUMENTS

| | | |
|---|---|---|
| 2009/0148387 A1 | 6/2009 | Bikram |
| 2009/0280063 A1 | 11/2009 | Kulkarni et al. |
| 2010/0260686 A1 | 10/2010 | Zhang et al. |
| 2010/0330368 A1 | 12/2010 | Prud'Homme et al. |
| 2011/0129417 A1* | 6/2011 | Hawkett ............ A61K 41/0052 424/1.61 |
| 2012/0190049 A1 | 7/2012 | Zhang et al. |
| 2012/0201760 A1 | 8/2012 | Tromsdorf et al. |
| 2013/0189367 A1 | 7/2013 | Zhang et al. |
| 2013/0261710 A1 | 10/2013 | Won et al. |
| 2013/0302252 A1 | 11/2013 | Zhang et al. |
| 2014/0161734 A1 | 6/2014 | Kim et al. |
| 2014/0271470 A1 | 9/2014 | Sillerud et al. |
| 2015/0037252 A1 | 2/2015 | Hawkett et al. |
| 2015/0125401 A1 | 5/2015 | Gendelman et al. |
| 2016/0158387 A1 | 6/2016 | Khnadhar et al. |
| 2016/0346389 A1 | 12/2016 | Friedman et al. |
| 2019/0125672 A1 | 5/2019 | Nie et al. |

FOREIGN PATENT DOCUMENTS

| | | |
|---|---|---|
| CN | 107715121 B | 1/2019 |
| EP | 2974745 A1 | 1/2016 |
| WO | WO-2011122770 A2 | 10/2011 |
| WO | WO-2013158549 A1 | 10/2013 |
| WO | WO-2013159092 A1 | 10/2013 |
| WO | WO-2015199555 A1 | 12/2015 |
| WO | WO-2016154552 A1 | 9/2016 |
| WO | WO-2021097537 A1 | 5/2021 |

OTHER PUBLICATIONS

Corem-Salkmon et al., Int. J. Nanomedicine, 2012, 7, p. 5517-5527. (Year: 2012).*
Pham et al., Int. J. Mol. Sci., 2018, 19, p. 1-23. (Year: 2018).*
Ishii et al., Chem. Commun., 2016, 52, 1517. (Year: 2016).*
Cardoso et al. What is the accuracy of sentinel lymph node biopsy for gastric cancer? A systematic review. Gastric Cancer 15(1):48-59 (2012).
Cooper et al. Positron emission tomography (PET) and magnetic resonance imaging (MM) for the assessment of axillary lymph node metastases in early breast cancer: systematic review and economic evaluation. Health Technology Assessment 15(4):iii (2011).
Hokkam et al. Assessment of Sentinel Lymph Node Biopsy in Colon Cancer and Its Impact on Staging. Journal of Surgery 4(2-1):36-40 (2016).
Huizing et al. Analysis of void artefacts in post-operative breast MM due to residual SPIO after magnetic SLNB in SentiMAG Trial participants. European Journal of Surgical Oncology 41(6):S18 (2015).
Kermani et al. Accuracy of sentinel node biopsy in the staging of non-small cell lung carcinomas: systematic review and meta-analysis of the literature. Lung Cancer 80(1):5-14 (2013).
Krischer et al. Feasibility of breast MM after sentinel procedure for breast cancer with superparamagnetic tracers. European Journal of Surgical Oncology 44(1):74-79 (2018).
Leinweber. Possible physiological roles of carboxylic ester hydrolases. Drug Metabolism Reviews 18(4):379-439 (1987).
Lenzo et al. Review of gallium-68 PSMA PET/CT imaging in the management of prostate cancer. Diagnostics 8(1):16 (2018).
Longmire et al. Clearance Properties of Nano-sized Particles and Molecules as Imaging Agents: Considerations and Caveats. Aranomedicine 3(5):703-717 (Oct. 2008).
Massart. Preparation of aqueous magnetic liquids in alkaline and acidic media. IEEE Transaction on Magnetics 17(2):1247-1248 (1981).
Muthiah et al. Mannose-poly(ethylene glycol)-linked SPION targeted to antigen presenting cells for magnetic resonance imaging on lymph node. Carbohydrate Polymers 92(2):1586-1595 (2013).
Niebling et al. Chapter 5: A systematic review and meta-analyses of sentinel lymph node identification in breast cancer and melanoma, a plea for tracer mapping. European Journal of Surgical Oncology (EJSO) 42(4):466-473 (2016).
PCT/AU2020/051264 International Search Report and Written Opinion dated Feb. 1, 2021.

(Continued)

*Primary Examiner* — Michael G. Hartley
*Assistant Examiner* — Leah H Schlientz
(74) *Attorney, Agent, or Firm* — WILSON SONSINI GOODRICH & ROSATI

(57) ABSTRACT

Disclosed herein are pharmacologically acceptable magnetic nanoparticles suitable for administration to a subject.

19 Claims, 8 Drawing Sheets

(56) References Cited

OTHER PUBLICATIONS

Siegel et al. Cancer statistics, 2019. A Cancer Journal For Clinicians 69(1):7-34 (2019).

Teshome et al. Use of a magnetic tracer for sentinel lymph node detection in early-stage breast cancer patients: a meta-analysis. Annals of Surgical Oncology 23(5):1508-1514 (2016).

Tse et al. PSMA-targeting iron oxide magnetic nanoparticles enhance MRI of preclinical prostate cancer. Nanomedicine 10(3):375-386 (2015).

Van Der Pas et al. Sentinel-lymph-node procedure in colon and rectal cancer: a systematic review and meta-analysis. The Lancet Oncology 12(6):540-550 (2011).

Ward et al. Focal therapy for the treatment of localized prostate cancer: a potential therapeutic paradigm shift awaiting better imaging. Current Opinion in Urology 22(2):104-108 (2012).

Weixler et al. Sentinel lymph node mapping with isosulfan blue or indocyanine green in colon cancer shows comparable results and identifies patients with decreased survival: a prospective single-center trial. World Journal of Surgery 41(9):2378-2386 (2017).

Winter. Magnetic resonance sentinel lymph node imaging and magnetometer-guided intraoperative detection in prostate cancer using superparamagnetic iron oxide nanoparticles. International Journal of Nanomedicine 13:6689-6698 (2018).

Clauson et al. Size-Controlled Iron Oxide Nanoplatforms with Lipidoid-Stabilized Shells for Efficient Magnetic Resonance Imaging-Trackable Lymph Node Targeting and High-Capacity Biomolecule Display. ACS Applied Materials & Interfaces 10:20281-20295 (2018).

Hellstern et al. Systemic Distribution and Elimination of Plain and with Cy3.5 Functionalized Poly(vinyl alcohol) Coated Superparamagnetic Maghemite Nanoparticles After Intraarticular Injection in Sheep In Vivo. J Nanosci Nanotechnol 6:3261-3268 (2006).

Mukherjee et al. Development and screening of a series of antibody-conjugated and silica-coated iron oxide nanoparticles for targeting the prostate-specific membrane antigen. ChemMedChem. 9(7):1356-60 (2014).

Prodrugs : Challenges and Rewards Part 1. Ed Stella et al. Springer Science & Business Media (pp. 160-171) (2007).

Zhan et al. In Vivo Dual-Modality Fluorescence and Magnetic Resonance Imaging-Guided Lymph Node Mapping with Good Biocompatibility Manganese Oxide Nanoparticles. Molecules 22(12):2208 (2017).

\* cited by examiner

MAGNETIC TRACER COMPOSITIONS

TECHNICAL FIELD

The present application relates to magnetic particles, compositions comprising the same and their use in diagnostic applications.

BACKGROUND

One of the most important prognostic/diagnostic factors for any solid tumour cancer is the stage of the cancer. For cancers that are confined to the primary tumour, surgery or ablation of the primary tumour alone is assumed to be curative. Therefore, knowing whether the cancer has spread to nearby lymph nodes, other lymph nodes, or distant sites is important to determine the patient's prognosis and to inform therapeutic pathways. Despite the curative therapy of surgery, many solid tumour cancers currently diagnosed as being localised are not cured by surgery alone and recur, with 5 year relative survival in the United States for localised cancer being only 45% for oesophageal cancer, 56% for lung and bronchial cancer, 69% for bladder cancer, 90% for colorectal cancer, and 92% for cervical cancer.

For most solid tumour cancers, preliminary staging is performed through non-invasive medical imaging, with options for radiology including Magnetic Resonance Imaging (MRI), Computed Tomography (CT), Positron Emission Tomography (PET), and Single Photon Emission Computed Tomography (SPECT). In general, these technologies are able to detect large metastasis in lymph nodes, with high specificity, but the sensitivity is relatively poor and ranges from 56% for PET/CT to 65% for MRI. The sensitivity of PET/CT drops to only 11% for micro-metastasis (metastasis of <2 mm). Ultra-small magnetic iron oxide nanoparticles (USPIONs) can be used as an MRI contrast agent, and show improved MRI sensitivity to 98%.

Due to the limitations of medical imaging, a second stage of diagnostic assessment is typically performed as part of surgery. The second stage may require the removal of many lymph nodes which are then assessed by pathology. The assessment of each lymph node will typically be standard hematoxylin-eosin (H&E) staining on a single dissection of the lymph node. This method has been shown to miss micro-metastasis in 15-44% of patients depending on the cancer. Improved surgical staging is possible if the sentinel lymph node is identified. The sentinel lymph node is the hypothetical first lymph node or nodes draining a cancer, and it is postulated they are the first organs reached by metastasized cancer cells. Therefore, they play an important role in the spread, diagnosis, and treatment of cancer, and it is postulated that if the sentinel node is free of tumour metastasis or isolated tumour cells the cancer is assumed to be localised and cured by removal of the primary tumour only.

In breast cancer and melanoma, the sentinel lymph node biopsy (SLNB) method has been shown to be accurate and reliable for staging patients clinically assessed as N0 by imaging, with very high sentinel node identification rates and low false negative rates (FNR). Sentinel lymph node biopsy involves injecting a tracer around a tumour and using imaging and surgical equipment to monitor the flow of the tracer through the lymph vessels to the sentinel nodes, and surgically removing the sentinel nodes for detailed analysis by pathology. The identification rate using Technetium-99m radioisotopes, lymphoscintigraphy imaging, and blue dye in breast cancer and melanoma is very high (96% to 100%), and the false negative rate was very low (1.5% to 2.6%). The success of SLNB in breast cancer and melanoma has resulted in significantly improved relative survival outcomes for patients diagnosed with localised disease in these cancers, with 5-year relative survivals of almost 100%.

In more complex cancers, problems with the technology and application of SLNB results in low identification rates and high false negative rates (FNR). Technetium-99m tracers are imaged using lymphoscintigraphy or SPECT/CT which have poor spatial resolution of ±10 to 15 mm. That results in a phenomenon called "shine-through" which masks sentinel nodes when they are close to the injection site and primary tumour, resulting in false negatives. In gastric cancer, the FNR is estimated to be 34.7%, 18.5%, and 13.1% for blue dye, radiolabelled colloid and a combination of the two techniques respectively. In lung cancer sentinel nodes are unable to be detected in an estimated 19.4% of patients, and sensitivity is 87%, with a false negative rate of 29.9%. In colorectal cancer false negative rates of SLNB are estimated to 25 and 36%.

Super-paramagnetic iron oxide nanoparticles (SPIONs), for example based on iron oxide particles coated with carboxy-dextran, have been applied to breast cancer SLNB and the technology has been shown to be non-inferior to radioisotopes and blue dye. That method is also assumed to overcome the spatial resolution issues of Technetium-99m. However, when applied to prostate cancer the number of nodes identified is approximately 18 due to the particles transitioning through the sentinel node into $2^{nd}$ and $3^{rd}$ echelon nodes. The use of SPIONs for identifying sentinel nodes remains ineffective for some applications.

Further, the development of effective magnetic nanoparticle-based diagnostics can be complicated by certain detrimental characteristics or behaviours of nanoparticles. For example, solutions or dispersions of nanoparticles generally have a tendency for the nanoparticles to agglomerate or aggregate and this then complicates or compromises the effectiveness of the diagnostic. Such aggregation can sometimes occur in-vivo, or after administration to the patient. Degradation of coatings from the SPION cores can also result in aggregation of the SPIONs at the injection site or collection of the particles in the liver and spleen, often remaining at the injection site for several years.

New non-surgical methods of staging cancer have been developed using PET molecular imaging, where PET isotopes are conjugated with molecules or monoclonal antibodies that have an affinity to specific cancer cells. Recently, PET-PSMA has been applied clinically in staging prostate cancer using an intra-venous injection, however this technology is not able to detect micro-metastasis in lymph nodes. Therefore, an extended pelvic lymph node dissection (ePLND) remains the gold standard in staging prostate cancer, despite being an aggressive surgery with significant side effects. One additional problem with PET targeted imaging, is the short half-life of the radioisotopes used (Gallium-68 at 68 minutes or Fluorine-18 at 109 minutes). Due to the short half-life this method of targeting cancer cells is limited to small ligands, as the circulation time of the tracer needs to be fast. Large monoclonal antibodies, such as J591 for prostate cancer, have long blood circulation times but are not viable with the preferred radioisotopes.

A possible alternative method for molecular targeted imaging is to use a peri-tumoural injection, and this may lead to improved detection of small metastasis due to the high volume of tracer transitioning through the lymph node. However, this method relies on the movement and clearance of the PET tracers through the entire lymph system, with only the tracer bound to the cancer cells remaining in the lymph nodes. The movement through the lymph system takes at least 24 hours for small ligands, and longer for monoclonal antibodies, and therefore this method is not viable for short half-life PET tracers.

Molecularly targeted PET tracers have also been applied to detecting primary lesions in various cancers such as prostate cancer. However, the limited spatial resolution of PET imaging only allows gross mapping of the primary lesion, insufficient for enabling accurate ablation of tumours under MRI, infrared, or optoacoustic guidance. For accurate ablation for focal therapy, a non-radioactive MRI compatible tracer is required.

The staging of cancer in many cancer indications unfortunately remains sub-optimal. While the use of SPIONs, Technetium-99m, dyes, and PET tracers have shown some promise, there are number of problems that still need to be addressed.

There remains a need for new materials/compositions and methods for staging cancer that overcome or ameliorate one or more of the disadvantages or shortcomings of prior art materials and methods. There is a particular need for materials/compositions that allow for the improved staging of cancer in the context of sentinel lymph node identification. Alternatively, or in addition, there is a need for materials/compositions and methods for staging cancer that provide a useful alternative to prior art materials and methods.

SUMMARY

The present invention provides pharmacologically acceptable magnetic nanoparticles suitable for administration to a subject, the magnetic nanoparticles having a pharmacologically acceptable polymer composition coating, the polymer composition comprising: (i) a polymeric steric stabiliser that promotes dispersion of the magnetic nanoparticles in a liquid, the polymeric steric stabiliser comprising (i) an anchoring polymer segment having one or more binding groups that bind the polymeric steric stabiliser to the magnetic nanoparticles, and (ii) a steric stabilising polymer segment comprising a polyacrylamide-co-polyalkylene oxide block copolymer, wherein the anchoring polymer segment is different from the steric stabilising polymer segment; and (ii) a polymeric targeting moiety comprising (i) an anchoring polymer segment having one or more binding groups that bind the polymeric targeting moiety to the magnetic nanoparticles, (ii) a linking polymer segment consisting of polyacrylamide, wherein the anchoring polymer segment is different from the linking polymer segment, and (iii) one or more targeting groups selected from a monosaccharide group for selectively targeting monosaccharide receptors, and antibodies, antibody fragments and inhibitors for selectively targeting Prostate Specific Membrane Antigen (PSMA).

The present invention also provides pharmacologically acceptable magnetic nanoparticles suitable for administration to a subject, the magnetic nanoparticles having a pharmacologically acceptable polymer composition coating, the polymer composition comprising: (i) a polymeric steric stabiliser that promotes dispersion of the magnetic nanoparticles in a liquid, the polymeric steric stabiliser comprising (i) an anchoring polymer segment having one or more binding groups that bind the polymeric steric stabiliser to the magnetic nanoparticles, and (ii) a steric stabilising polymer segment having from 10 to 70 polymerised monomer residue units, wherein the anchoring polymer segment is different from the steric stabilising polymer segment; and (ii) a polymeric targeting moiety comprising (i) an anchoring polymer segment having one or more binding groups that bind the polymeric targeting moiety to the magnetic nanoparticles, (ii) a linking polymer segment having from 15 to 100 polymerised monomer residue units, wherein the anchoring polymer segment is different from the linking polymer segment and the linking polymer segment has more polymerised monomer residue units than the steric stabilising polymer segment, and (iii) one or more targeting groups selected from a monosaccharide group for selectively targeting monosaccharide receptors, and antibodies, antibody fragments and inhibitors for selectively targeting Prostate Specific Membrane Antigen (PSMA).

In one embodiment, the polymer composition further comprises (iii) a polymeric luminescent moiety comprising (i) an anchoring polymer segment having one or more binding groups that bind the polymeric luminescent moiety to the magnetic nanoparticles, (ii) a linking polymer segment, wherein the anchoring polymer segment is different from the linking polymer segment, and (iii) one or more luminescent groups for emitting light or an acoustic signal in response to light that enables in vivo location visualisation of the magnetic nanoparticles.

The pharmacologically acceptable magnetic nanoparticles according to the invention may form part of a composition suitable for administration to a subject.

When used for sentinel lymph node mapping, the pharmacologically acceptable magnetic nanoparticles or compositions comprising them according to the invention advantageously support high resolution MRI imaging, are retained more efficiently in sentinel nodes, and/or can be readily identified with existing surgical equipment such as infrared cameras and existing magnetometers. Furthermore, when used for targeting cancer in lymph nodes or primary tumours, the pharmacologically acceptable magnetic nanoparticles or compositions comprising them according to the invention have improved binding to cancer cells over existing SPIONs, are advantageously non-radioactive, not dependent on short circulation times or lymph clearance times, have high spatial resolution to support peri-tumoural injections, have improved blood half-life to support systemic injections, and/or do not substantially degrade in-vivo.

Without wishing to be limited by theory, it is believed the pharmacologically acceptable magnetic nanoparticles according to the invention exhibit their advantageous properties at least through the unique polymer composition coating the magnetic nanoparticles. That polymer composition coating comprises at least a steric stabiliser that promotes dispersion of the magnetic nanoparticles in a liquid in combination with a polymeric targeting moiety. Both the steric stabiliser and the polymeric targeting moiety comprise an anchoring polymer segment that bind the respective entities to the magnetic nanoparticles. Those anchoring polymer segments have advantageously been found to be highly effective at maintaining both the steric stabiliser and polymeric targeting moiety secured to the magnetic nanoparticles when, for example, located in an in vivo liquid environment. That in turn facilitates maintaining the magnetic nanoparticles in a dispersed form within that in vivo liquid environment. Those skilled in the art will appreciate aggregation of the magnetic nanoparticles in an in vivo liquid environment would be detrimental in diagnostic applications.

The polymer composition coating of the magnetic nanoparticles is also believed to play a key role in their improved ability to be retained in sentinel nodes. Working in synergy with the imparted effect of improved dispersion within, for example, an in vivo liquid environment, again without wishing to be limited by theory, it is believed the dual role played by the steric stabiliser and polymeric targeting moiety of the polymer composition coating creates a surface environment that is less prone to protein adsorption and subsequent cell uptake in macrophages. Those skilled in the art will appreciate such protein adsorption to the magnetic nanoparticles reduces targeting efficiency, which in turn increases transfer through sentinel nodes into echelon nodes. Surprisingly, it is believed that the polymer composition coating affords to the magnetic nanoparticles a unique combination of improved dispersion ability and stealth properties that synergistically enhance targeting efficiency, the effect of which has been found to improve retention of the magnetic nanoparticles in sentinel nodes.

It has been found one or more advantages that can be derived from the present invention can be modulated through the selection of the polymer composition that makes up at least the steric stabilising and linking polymer segments and/or the selection of the number of polymerised monomer residue units that make up the steric stabilising and linking polymer segments.

The present invention therefore also provides a composition suitable for administration to a subject, the composition comprising the pharmacologically acceptable magnetic nanoparticles according to the invention.

The compositions in accordance with the invention may present the pharmacologically acceptable magnetic nanoparticles in a pharmacologically acceptable liquid carrier.

The present invention further provides a composition suitable for administration to a subject, the composition comprising the pharmacologically acceptable magnetic nanoparticles according to the invention in a pharmacologically acceptable liquid carrier.

The present invention provides a composition suitable for administration to a subject, the composition comprising pharmacologically acceptable magnetic nanoparticles (i) having a pharmacologically acceptable polymer composition coating, and (ii) in a pharmacologically acceptable liquid carrier, the polymer composition comprising: (i) a polymeric steric stabiliser that promotes dispersion of the magnetic nanoparticles in the liquid carrier, the polymeric steric stabiliser comprising (i) an anchoring polymer segment having one or more binding groups that bind the polymeric steric stabiliser to the magnetic nanoparticles, and (ii) a steric stabilising polymer segment comprising a polyacrylamide-co-polyalkylene oxide block copolymer, wherein the anchoring polymer segment is different from the steric stabilising polymer segment; and (ii) a polymeric targeting moiety comprising (i) an anchoring polymer segment having one or more binding groups that bind the polymeric targeting moiety to the magnetic nanoparticles, (ii) a linking polymer segment consisting of polyacrylamide, wherein the anchoring polymer segment is different from the linking polymer segment, and (iii) one or more targeting groups selected from a monosaccharide group for selectively targeting monosaccharide receptors, and antibodies, antibody fragments and inhibitors for selectively targeting Prostate Specific Membrane Antigen (PSMA).

The present invention also provides a composition suitable for administration to a subject, the composition comprising pharmacologically acceptable magnetic nanoparticles (i) having a pharmacologically acceptable polymer composition coating, and (ii) in a pharmacologically acceptable liquid carrier, the polymer composition comprising: (i) a polymeric steric stabiliser that promotes dispersion of the magnetic nanoparticles in the liquid carrier, the polymeric steric stabiliser comprising (i) an anchoring polymer segment having one or more binding groups that bind the polymeric steric stabiliser to the magnetic nanoparticles, and (ii) a steric stabilising polymer segment having from 10 to 70 polymerised monomer residue units, wherein the anchoring polymer segment is different from the steric stabilising polymer segment; and (ii) a polymeric targeting moiety comprising (i) an anchoring polymer segment having one or more binding groups that bind the polymeric targeting moiety to the magnetic nanoparticles, (ii) a linking polymer segment having from 15 to 100 polymerised monomer residue units, wherein the anchoring polymer segment is different from the linking polymer segment and the linking polymer segment has more polymerised monomer residue units than the steric stabilising polymer segment, and (iii) one or more targeting groups selected from a monosaccharide group for selectively targeting monosaccharide receptors, and antibodies, antibody fragments and inhibitors for selectively targeting Prostate Specific Membrane Antigen (PSMA).

The one or more targeting groups will of course be for selectively targeting monosaccharide receptors or Prostate Specific Membrane Antigen (PSMA) in the subject upon administration of the magnetic nanoparticles or composition comprising them.

The present invention further provides use of the pharmacologically acceptable magnetic nanoparticles according to the invention or the composition according to the invention for performing a diagnostic application on a subject.

Examples of suitable diagnostic applications include magnetic resonance imaging, cancer surgery and visualising lymph node metastases.

The pharmacologically acceptable magnetic nanoparticles and compositions according to the invention can be used in conjunction with in vivo imaging techniques including, but not limited to, ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

The pharmacologically acceptable magnetic nanoparticles and compositions according to the invention can advantageously enable detection of tissue, such as lymph nodes, that have retained the nanoparticles following administration to a subject. That detection can be used to identify tissue that could be affected by certain forms of cancer. The pharmacologically acceptable magnetic nanoparticles have advantageously been found to demonstrate improved retention in sentinel lymph nodes. As those skilled in the art will appreciate, the sentinel lymph node is the hypothetical first lymph node or group of nodes draining a cancer. It is therefore postulated the sentinel lymph node(s) is the target organ primarily reached by metastasizing cancer cells from tumours. The pharmacologically acceptable magnetic nanoparticles can therefore offer improved cancer staging through detection of sentinel lymph nodes and use as part of a SLNB procedure comprising the identification, removal and analysis of the sentinel lymph nodes associated with a particular tumour.

The present invention also provides use of the pharmacologically acceptable magnetic nanoparticles and compositions according to the invention for in vivo imaging.

The present invention also provides pharmacologically acceptable magnetic nanoparticles and compositions according to the invention for use in in vivo imaging.

The present invention also provides the pharmacologically acceptable magnetic nanoparticles and compositions according to the invention for use in the detection of cancer.

The present invention further provides use of the pharmacologically acceptable magnetic nanoparticles and compositions according to the invention for detection of sentinel lymph nodes.

The present invention also provides the pharmacologically acceptable magnetic nanoparticles and compositions according to the invention for use in the detection of sentinel lymph nodes.

The present invention also provides a method for the detection of cancer in a subject, the method comprising: administering the pharmacologically acceptable magnetic nanoparticles or the composition according to the invention to the subject: and detecting the magnetic nanoparticles, wherein the localisation of magnetic nanoparticles indicates the presence of tissue affected by cancer in the subject.

The present invention further provides a method for the treatment of a subject with cancer, the method comprising: administering the pharmacologically acceptable magnetic nanoparticles or the composition according to the invention to the subject; detecting the magnetic particles; identifying the subject as having cancer, wherein the localisation of magnetic particles indicates the presence of tissue affected by cancer in the subject; and treating a subject identified as having cancer in (iii) with a treatment for cancer.

Further aspects and embodiment of the invention are outlined and discussed in more detail below.

BRIEF DESCRIPTION OF THE FIGURES

Embodiments of the present disclosure will be discussed with reference to the accompanying non-limiting figures wherein.

DETAILED DESCRIPTION

Figure 1:
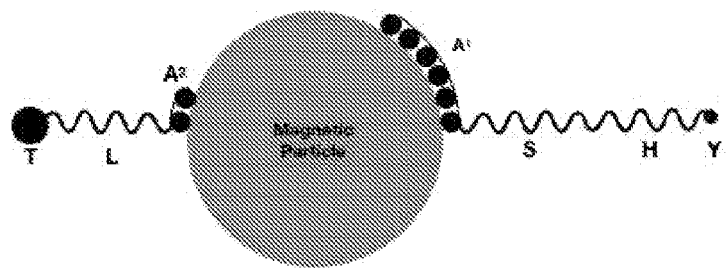
FIG. 1 is a schematic showing a coated nanoparticle according to embodiments of the present disclosure.
Figure 2:
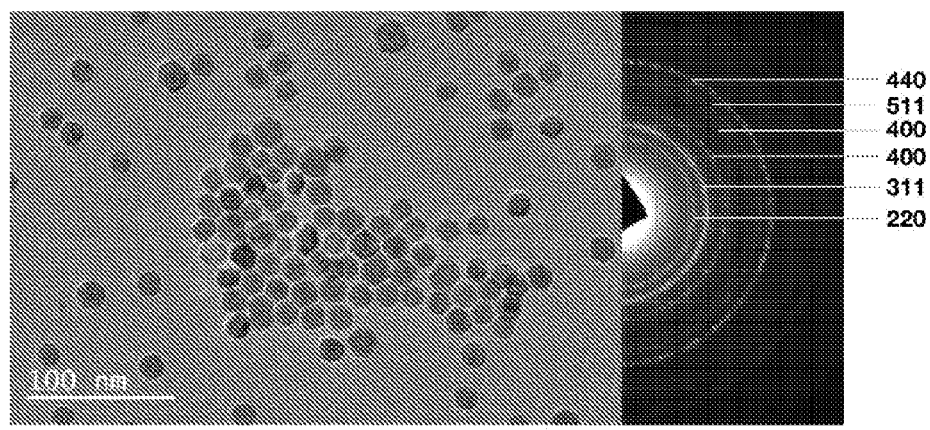
FIG. 2 shows a transmission electron micrograph and selected area diffraction (indexed to magnetite) of coated nanoparticles synthesised as per Example 1.
Figure 3:
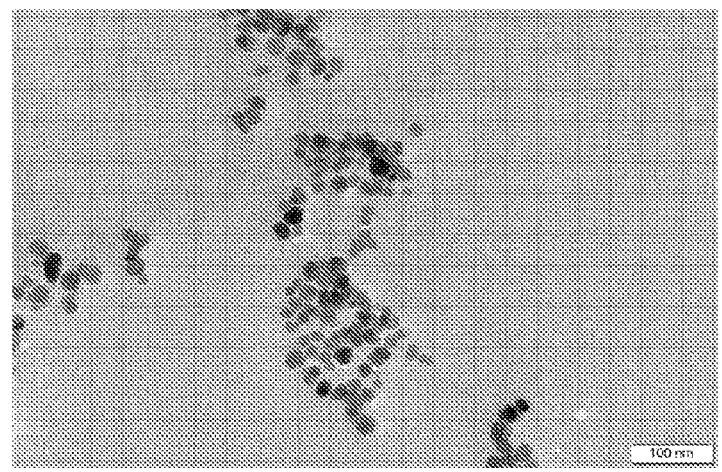
FIG. 3 shows a transmission electron micrograph of coated nanoparticles produced as per Example 2.
Figure 4:
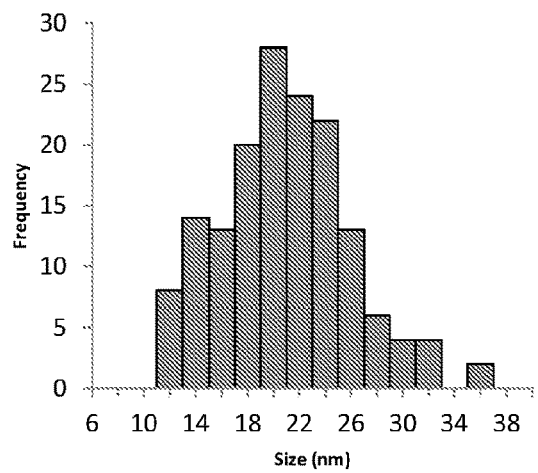
FIG. 4 shows the particle size distribution (from TEM) of coated nanoparticles produced as per Example 2.
Figure 5:
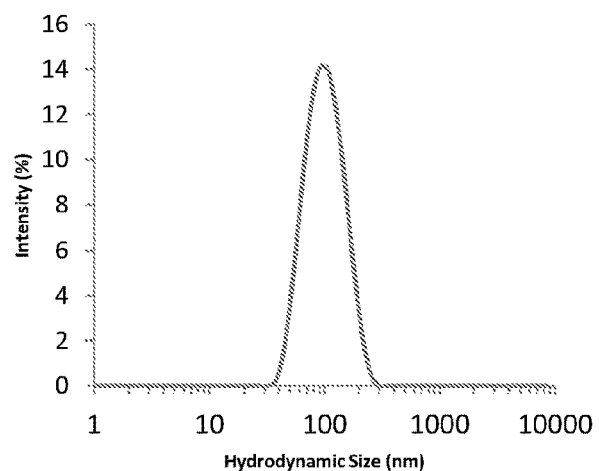
FIG. 5 shows the hydrodynamic size distribution (from dynamic light scattering) of coated nanoparticles produced as per Example 2.
Figure 6:
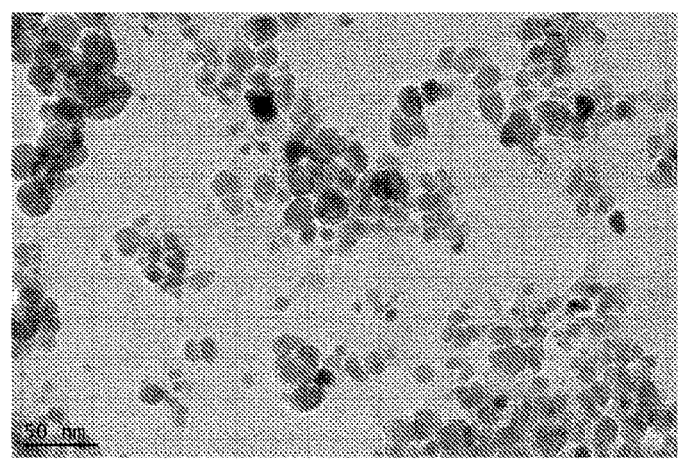
FIG. 6 shows a transmission electron micrograph of coated nanoparticles synthesised as per Example 5.
Figure 7:
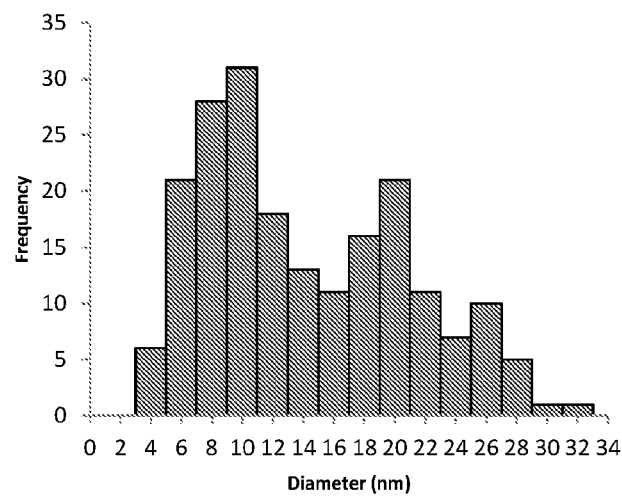
FIG. 7 shows the particle size distribution (from TEM) of coated nanoparticles produced as per Example 5.
Figure 8:
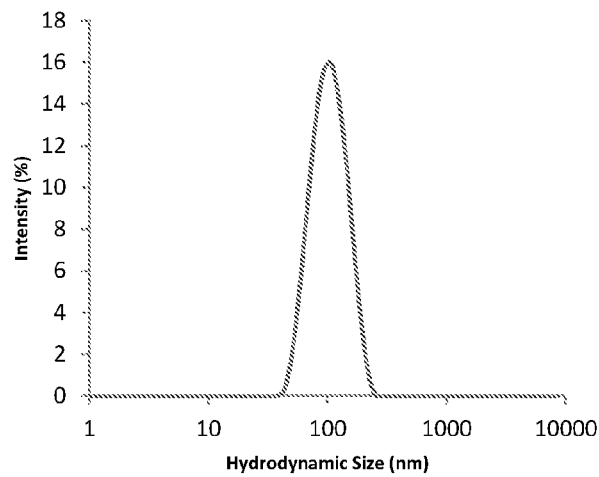
FIG. 8 shows the hydrodynamic size distribution (from dynamic light scattering) of coated nanoparticles produced as per Example 5.
Figure 9:
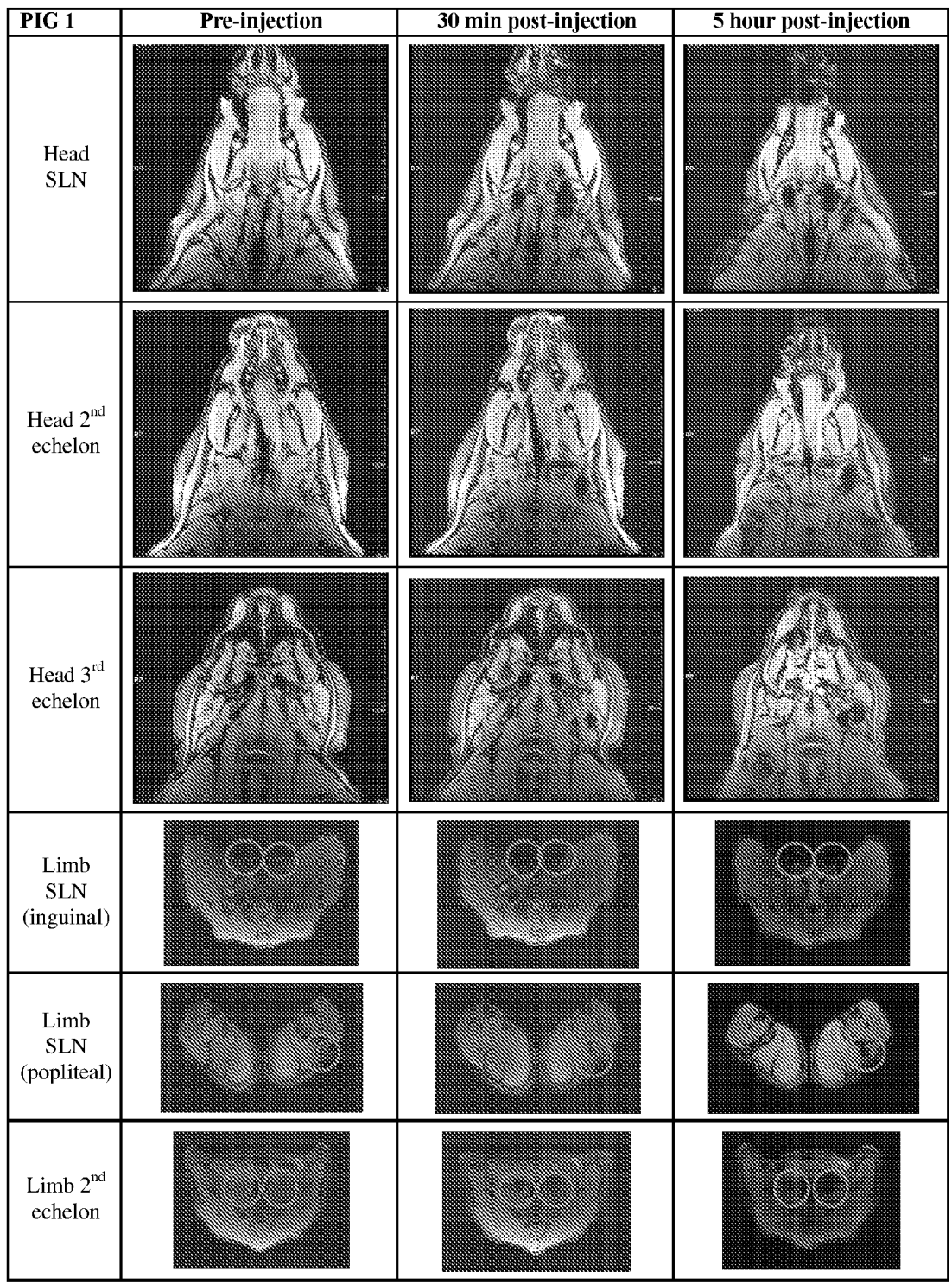
FIG. 9 shows MRI scans of a first swine showing uptake into the sentinel lymph node over 30 minutes and 5 hours.
Figure 10:
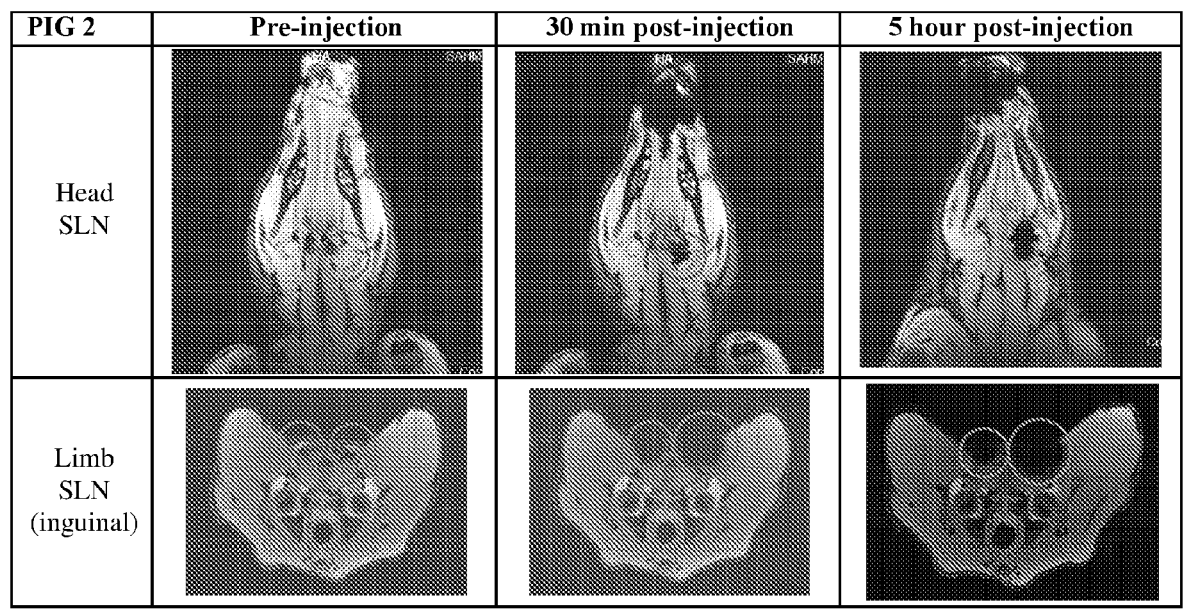
FIG. 10 shows MRI scans of a second swine showing uptake into the sentinel lymph node over 30 minutes and 5 hours.
Figure 11:
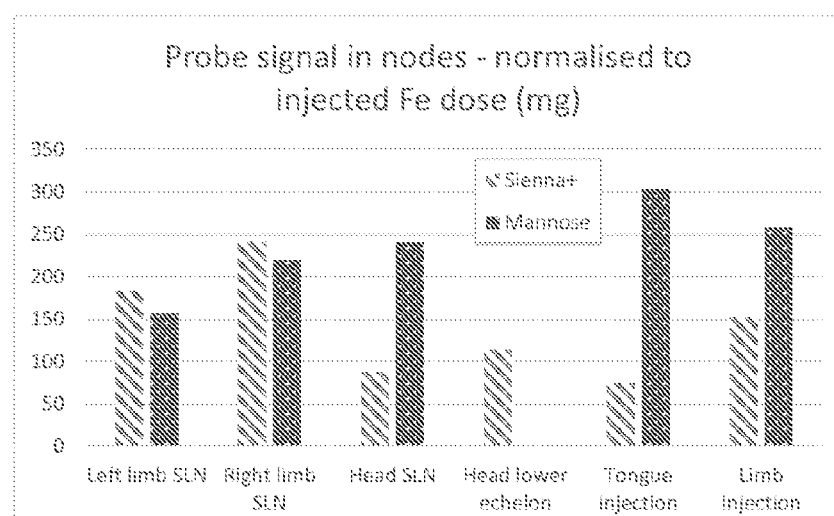
FIG. 11 is a series of plots showing probe signal in nodes normalised to injected Fe dose (mg) for Sienna+® nanoparticles (blue left bars) and mannose coated nanoparticles (red right bars)
Figure 12:
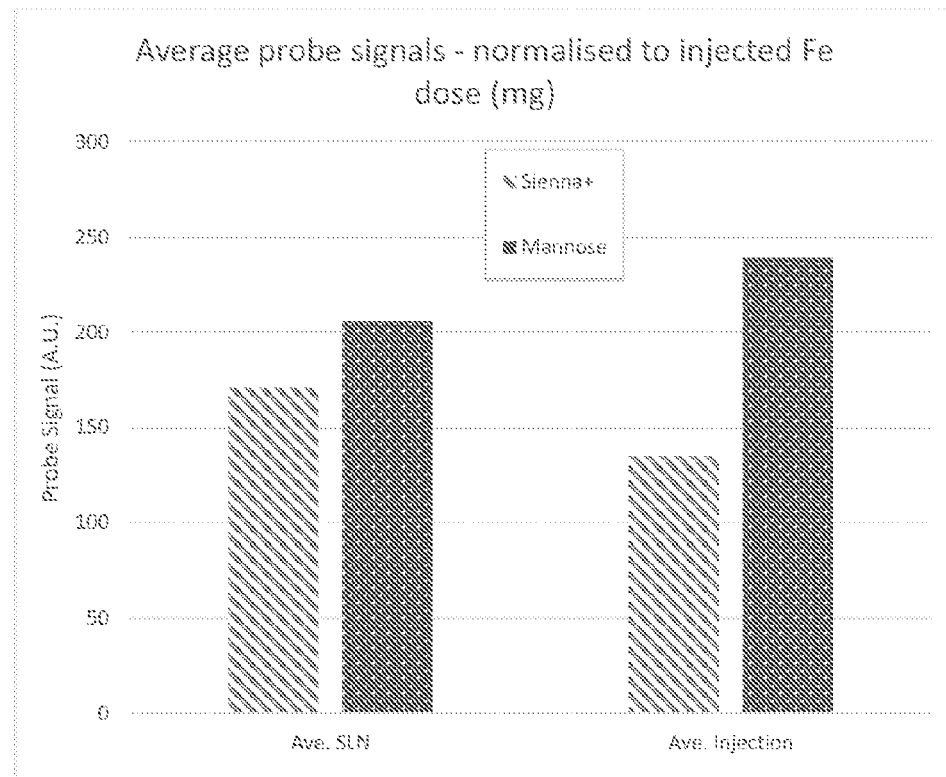
FIG. 12 shows a plot of average probe signals normalised to injected Fe dose (mg) for Sienna+® nanoparticles (blue left bars) and mannose coated nanoparticles (red right bars)

In this specification a number of terms are used which are well known to a skilled addressee. Nevertheless for the purposes of clarity a number of terms will be defined.

The pharmacologically acceptable magnetic nanoparticles according to the invention have a pharmacologically acceptable polymer composition coating. For convenience, those pharmacologically acceptable magnetic nanoparticles may herein be simply described as the "coated nanoparticles".

As used herein, the term "unsubstituted" means that there is no substituent or that the only substituents are hydrogen.

The term "optionally substituted" as used throughout the specification denotes that the group may or may not be further substituted or fused (so as to form a condensed poly cyclic system), with one or more non-hydrogen substituent group. In certain embodiments the substituent groups are one or more group independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl, wherein R$^a$, R$^b$, R$^c$ and R$^d$ are each independently selected from the group consisting of H, C$_1$-C$_{12}$alkyl, C$_1$-C$_{12}$haloalkyl, C$_2$-C$_{12}$alkenyl, C$_2$-C$_{12}$alkynyl, C$_2$-C$_{10}$ heteroalkyl, C$_3$-C$_{12}$cycloalkyl, C$_3$-C$_{12}$cycloalkenyl, C$_2$-C$_{12}$heterocycloalkyl, C$_2$-C$_{12}$heterocycloalkenyl, C$_6$-C$_{18}$aryl, C$_2$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

Alternatively, two optional substituents on the same moiety when taken together may be joined to form a fused cyclic substituent attached to the moiety that is optionally substituted. Accordingly the term optionally substituted includes a fused ring such as a cycloalkyl ring, a heterocycloalkyl ring, an aryl ring or a heteroaryl ring.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Alkyl" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ alkyl unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Amino acid" and variations of that term used herein includes the twenty naturally occurring amino acids shown in the table below; those amino acids often modified post-translationally in vivo, including, for example, hydroxyproline, phosphoserine and phosphothreonine; and other non-natural amino acids. Furthermore, the term "amino acid" includes both D- and L-amino acids.

| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_5$-$C_7$ cycloalkyl or $C_5$-$C_7$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Halogen" refers to chlorine, fluorine, bromine or iodine.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed. The isomeric forms such as diastereomers, enantiomers, and geometrical isomers can be separated by physical and/or chemical methods known to those skilled in the art.

Additionally, the formulas and compositions described herein are intended to cover, where applicable, solvated as well as unsolvated forms of compounds. Thus, each formula includes compounds having the indicated structure, including the hydrated as well as the non-hydrated forms.

The term "about" or "approximately" means within an acceptable range for the particular value as determined by one of ordinary skill in the art, which will depend in part on how the value is measured or determined, e.g. the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value, such as ±1-20%, preferably ±1-10% and more preferably ±1-5%.

Where a range of values is provided, it is understood that each intervening value, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

A phrase referring to "at least one of" a list of items refers to any combination of those items, including single members. As an example, "at least one of: a, b, or c" is intended to cover: a, b, c, a-b, a-c, b-c, and a-b-c.

The term "pharmaceutically acceptable salts" refers to salts that retain the desired biological activity of the above-identified compounds and include pharmaceutically acceptable acid addition salts and base addition salts. Suitable pharmaceutically acceptable acid addition salts of compounds of formula I may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton. PA 1995. In the case of agents that are solids, it is understood by the skilled person that the compounds, agents and salts may exist in different crystalline or polymorphic forms, all of which are intended to be within the scope of the present disclosure and specified formulae.

"Prodrug" means a compound that undergoes conversion to a desired compound within a biological system, usually by metabolic means (e.g. by hydrolysis, reduction or oxidation). For example an ester prodrug of a compound containing a hydroxyl group may be convertible by hydrolysis in vivo to the parent molecule. Suitable esters of compounds containing a hydroxyl group, are for example acetates, citrates, lactates, tartrates, malonates, oxalates, salicylates, propionates, succinates, fumarates, maleates, methylene-bis-P-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound containing a carboxy group may be convertible by hydrolysis in vivo to the parent molecule. Examples of ester prodrugs are those described by Leinweber. 1987. Similarly, an acyl prodrug of a compound containing an amino group may be convertible by hydrolysis in vivo to the parent molecule. Examples of prodrugs for these and other functional groups, including amines, are provided in Borchardt et al., 2007.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state. The effective amount may vary depending upon the health and physical condition of the subject to be treated, the taxonomic group of subject to be treated, the degree of result desired, the formulation of the composition, the assessment of the medical situation, and other relevant factors. It is expected that the effective amount will fall in a relatively broad range that can be determined through routine trials.

The term "functional equivalent" is intended to include variants of the compounds described herein. For example, it will be understood that peptides and proteins may have isoforms, such that while the primary, secondary, tertiary or quaternary structure of a given peptide or protein isoform is different to the prototypical peptide or protein, the molecule maintains biological activity. Isoforms may arise from normal allelic variation within a population and include mutations such as amino acid substitution, deletion, addition, truncation, or duplication. Also included within the term "functional equivalent" are variants generated at the level of transcription.

The coated nanoparticles described herein are suitable for administration to a subject. The ten "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human. In certain embodiments, the coated nanoparticles are formulated for injection into tissue.

The coated nanoparticles described herein are pharmacologically acceptable which means they are compatible with other ingredients of any composition containing the coated nanoparticles, and they are suitable for use in contact with the tissue or organ of a subject to whom they are administered without excessive toxicity, irritation, allergic response, immunogenicity, or other problems or complications, commensurate with a reasonable benefit/risk ratio.

By "pharmacologically acceptable" in general is meant that the coated nanoparticles, the coating polymer composition, a liquid carrier, or other constituent of the composition is suitable for administration to a subject in their own right. In other words, administration of the coated nanoparticles, liquid carrier or other constituent of the composition to a subject will not result in unacceptable toxicity, including allergenic responses and disease states.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Having said that, those skilled in the art will appreciate that the suitability of the coated nanoparticles or composition comprising them for administration to a subject and whether or not a given constituent component would be considered pharmacologically acceptable, will to some extent depend upon the mode of administration selected. Thus, the mode of administration may need to be considered when evaluating whether a given composition is suitable for administration to a subject or pharmacologically acceptable.

The coated nanoparticles or composition comprising them may be administered to a subject by any suitable means, including intravenously, intraperitoneally, subcutaneously, intracranially, intradermally, intramuscularly, intraoccularly, intrathecally, intracereberally and intranasally. The coated nanoparticles or composition comprising them may also be administered directly into a tumour and/or into tissue adjacent one or more segments of a tumour.

The coated nanoparticles may be provided in a form suitable for injectable use and include, for example, sterile aqueous dispersions and sterile powders for the extemporaneous preparation of sterile injectable dispersions.

The magnetic "nanoparticles" are submicron particles having at least one dimension less than about 200 nm, or about 150 nm or about 100 nm. In one embodiment, all dimensions of the magnetic nanoparticles are less than about 100 nm.

The magnetic nanoparticles may be in the form of primary particles, or in the form or an aggregation of primary particles. In one embodiment, they are in the form of primary particles.

For avoidance of any doubt, reference herein to the "size" of the magnetic nanoparticles is intended to denote an average size (at least about 50 number %) of the particles based on the largest dimension of a given particle.

The size of the magnetic nanoparticles per se is determined herein by Transmission Electron Microscopy (TEM).

For avoidance of any doubt, when the magnetic nanoparticles are in the form of an aggregation of primary particles, reference to the size of such material is intended to be a reference to the largest dimension of the aggregate not the primary particles that form the aggregate.

In some embodiments, when the magnetic nanoparticles form aggregates, the size of the aggregates may exceed 100 nm.

The magnetic nanoparticles will generally be of a size that is less than about 100 nm, less than about 50 nm, or less than about 25 nm.

In certain embodiments, the magnetic nanoparticles have a size that is less than about 50 nm in at least one dimension. In certain embodiments, the magnetic nanoparticles have a particle size that ranges from about 10 nm to about 80 nm, or about 10 nm to about 50 nm, or about 25 nm to about 30 nm in at least one or all dimensions.

In one embodiment, magnetic nanoparticles have a size that is about: 6, 8, 10, 15, 20, 30, 40, 50, 60, 70, 80, 90 or 100 nm.

The nanoparticles used in accordance with the invention are magnetic. The magnetic nanoparticles generally exhibit ferromagnetic, ferrimagnetic or superparamagnetic properties.

The magnetic nanoparticles will be made of or comprise magnetic material.

Examples of suitable magnetic materials include, but are not limited to, iron, nickel, chromium, cobalt, gadolinium, oxides or oxyhydroxides of any of the aforementioned, and mixtures of any of the aforementioned. In certain embodiments, the magnetic nanoparticles comprises iron and/or an oxide or oxyhydroxide thereof. Suitable iron oxide magnetic materials include maghemite ($\gamma$-$Fe_2O_3$) and magnetite ($Fe_3O_4$).

In one embodiment, the magnetic nanoparticles comprise one or more of iron, nickel, chromium, cobalt, gadolinium, and oxides or oxyhydroxides thereof.

In another embodiment, the magnetic nanoparticles comprise iron (Fe), maghemite ($\gamma$-$Fe_2O_3$), magnetite ($Fe_3O_4$) or a combination thereof.

In some embodiments, the magnetic nanoparticles are or comprise magnetite ($Fe_3O_4$) or maghemite ($\gamma$-$Fe_2O_3$) with a particle size less than 50 nm, for example between 1 and 40 nm.

The magnetic nanoparticles may be in the form of a metal, such as iron, surrounded by a magnetic metal oxide shell, such as a maghemite ($\gamma$-$Fe_2O_3$) shell around the core.

In some embodiments, the magnetic nanoparticles are or comprise ferrites of general formula $MO \cdot Fe_2O_3$ where M is a bivalent metal such as Fe, Co, Ni, Mn, Be, Mg, Ca, Ba, Sr, Cu, Zn, Pt, Gd or mixtures thereof, or magnetoplumbite type oxides of the general formula $MO \cdot 6Fe_2O_3$ where M is a large bivalent ion, metallic iron, cobalt or nickel. Additionally, they could be particles of pure Fe, Zn, Ni, Cr, Co or Gd or oxides or oxyhydroxides of those. Alternatively they could be mixtures of any of those.

In some applications, it may be desirable to use magnetic nanoparticles that are superparamagnetic. As used herein, the term "superparamagnetic" is intended to mean magnetic material that does not have the following properties; (i) coercivity, (ii) remanence, or (iii) a hysteresis loop when the rate of change of an applied magnetic field is quasi-static.

The magnetic nanoparticles have a polymer composition coating as described herein. The coated nanoparticles may therefore be described as having a magnetic material core with a polymer composition coating.

The coated nanoparticles may also be described as having a metal core. The metal core may be or comprise any type of magnetic material.

The magnetic nanoparticles are coated or surrounded by a pharmacologically acceptable polymer composition coating. In that context, the terms "coated", "coating" or "surrounded by" means that the polymer composition covers or surrounds at least part of the outer surface of the magnetic material core and interacts with its surroundings. Polymeric steric stabiliser and targeting moiety constituent components of the pharmacologically acceptable polymer composition coating (discussed in more detail below) bind to the magnetic material core through anchoring polymer segments.

Magnetic nanoparticles used in accordance with the invention may conveniently be prepared using techniques known in the art.

In accordance with the invention, a polymeric steric stabiliser promotes dispersion of the magnetic nanoparticles in a liquid. By "promotes" in that context is meant that in the absence of the polymeric steric stabiliser the magnetic nanoparticles would otherwise flocculate, aggregate or settle out from the liquid carrier as sediment. In other words, the polymeric steric stabiliser functions to maintain the magnetic nanoparticles in a dispersed state within the liquid.

By being a polymeric "steric" stabiliser is meant that dispersion of the magnetic nanoparticles in a liquid occurs as a result of steric repulsion forces. Having said this, the polymeric steric stabiliser may present electrostatic repulsion forces that also assist with stabilisation of the polymeric. However, those skilled in the art will appreciate that such electrostatic forces will provide little if any stabilising function in liquids having a relatively high ionic strength. The steric stabilising function of the polymeric steric stabiliser used in accordance with the invention therefore plays an important role in enabling the magnetic nanoparticles to be maintained or remain stable in a dispersed state in the liquid.

The polymeric steric stabiliser used in accordance with the invention has been found to be particularly effective promoting dispersion of the magnetic nanoparticles in liquids, in particular in an in vivo liquid environment.

A number of constituent components of the polymer composition coating used in accordance with the invention are polymeric or have a polymer segment. By being "polymeric" or having a "polymer segment" is meant that component comprises a polymer chain derived from the polymerisation of monomers. Accordingly, the polymeric component or polymer segment will comprise or be made of polymerised monomer residue units. The polymeric component or polymer segment can be prepared by any suitable polymerisation technique. In one embodiment, a polymer segment (e.g. anchoring, steric stabilising and linking) described herein is prepared by the polymerisation of ethylenically unsaturated monomer. The polymer chains may (and some do) have non-polymeric components covalently attached to them, for example targeting or luminescent groups.

The present invention also provides pharmacologically acceptable coated nanoparticles suitable for administration to a subject for use in diagnostic and/or therapeutic applications, the coated nanoparticles comprising a metal core surrounded by a pharmacologically acceptable polymer composition coating, the polymer composition coating comprising:

a polymeric steric stabiliser that promotes dispersion of the nanoparticles in liquid, the steric stabiliser comprising (i) an anchoring polymer segment having one or more binding group that binds the steric stabiliser to the metal core, and (ii) a steric stabilising polymer segment; and one or both of:

a polymeric targeting moiety comprising (i) an anchoring polymer segment having one or more binding group that binds the targeting moiety to the metal core, and (ii) one or more targeting group for selectively targeting specific receptors in the subject upon administration of the dispersion; and a polymeric luminescent moiety comprising (i) an anchoring polymer segment having one or more binding group that bind the luminescent moiety to the nanoparticles, and (ii) one or more luminescent group for emitting light or an acoustic signal in response to light that enables in vivo location visualisation of the nanoparticles.

In some embodiments, the polymeric targeting and luminescent moieties do not comprise the steric stabilising polymer segment used in the steric stabiliser.

The polymeric targeting and luminescent moieties may each comprise a linking polymer segment.

The polymeric steric stabiliser used in accordance with the invention comprises a steric stabilising polymer segment.

The steric stabilising polymer segment may comprise polyacrylamide (PA), polyvinyl alcohol (PVA), polyalkylene oxide (e.g. polyethylene oxide (PEO), polypropylene oxide (PPO)), polyoxamers, polyhydroxyethylacrylate, poly-N-isopropylacrylamide, polydimethylamino-ethylmethacrylate, polyvinyl pyrrolidone (PVP), polyacrylicacid (PAA), polyacrylate, polymethacrylate, polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of two or more of the aforementioned.

Where the steric stabilising polymer segment comprises polyalkylene oxide the polyalkylene oxide may be selected from polyethylene glycol, polypropylene glycol and derivatives thereof. The polyalkylene oxide polymer may be end capped with an alkyl group. The alkyl group may be a $C_1$ to $C_6$ alkyl group, such as a methyl group, an ethyl group, a propyl group or an isopropyl group.

The steric stabilising polymer segment will generally comprise less than about 70 polymerised monomer residue units and, in certain embodiments, has from about 40 to about 60 polymerised monomer residue units, such as about 50 polymerised monomer residue units that make up the overall polymer segment.

In some embodiments, the steric stabilising polymer segment comprises from about 10 to about 70 polymerised monomer residue units.

The steric stabilising polymer segment may be a homopolymer or a copolymer.

In one embodiment, the steric stabilising polymer segment comprises or consists of a polyacrylamide-co-polyalkylene oxide block copolymer. That block copolymer may comprise or consist of about 8 to about 60 polymerised acrylamide units and about 2 to about 10 polymerised alkylene oxide units.

In another embodiment, the steric stabilising polymer segment comprises from about 10 to about 13 polymerised alkylene oxide units.

Those skilled in the art will appreciate polymerised alkylene oxide units provide for poly alkylene oxide.

The polymeric steric stabiliser, polymeric targeting moiety and polymeric luminescent moiety used in accordance with the invention each comprise an anchoring polymer segment.

By an "anchoring polymer segment" is meant a segment or region of the given polymeric entity (i.e. polymeric steric stabiliser, polymeric targeting moiety and polymeric luminescent moiety) that is a polymer chain, has an affinity toward the surface of the magnetic nanoparticles and functions to secure the given entity to the magnetic nanoparticles through one or more binding groups. The one or more binding group form part of the polymer chain backbone or they may be pendant to the polymer chain backbone. A binding group can be any element or molecule with a binding affinity for the magnetic nanoparticles. For example, the binding group can be any element or molecule with a binding affinity for iron or iron oxide. Suitable binding groups that can be used include groups comprising one or more phosphorous (P) atom, groups comprising one or more oxygen (O) atom, groups comprising one or more sulfur (S) atom, groups comprising one or more nitrogen (N) atom, and groups comprising any two or more of the aforementioned atoms.

In one embodiment, the anchoring polymer segment comprises one or more binding groups selected from phosphate groups, phosphonate groups, dimercaptosuccinic acid (DMSA) groups, sulfate groups, sulfonate groups, catechol groups, carboxylate groups, amine groups, and silane groups.

By being a polymer segment, it will be appreciated the anchoring segment comprises polymerised monomer residues. In particular, the segment will comprise polymerised monomer residues that give rise to the required binding affinity toward the magnetic nanoparticles. The polymerised monomer residues that make up the anchoring polymer segment may be the same or different.

It is believed that the ability of the anchoring segment to present multiple sites for binding interactions with the magnetic nanoparticles at least in part gives rise to the excellent stabilising properties provided by the polymeric steric stabiliser.

The anchoring segment may have at least two polymerised monomer residues that each provides a site for binding with the magnetic nanoparticles, or at least three, or at least five, or at least seven, or at least ten of such polymerised monomer residues. Not all of the polymerised monomer residues that make up the anchoring segment are necessarily required to give rise to a binding interaction with the magnetic nanoparticles, but it is generally preferred that the majority if not all of the polymerised monomer residues that make up the anchoring segment do give rise to a binding interaction with the magnetic nanoparticles.

The anchoring polymer segment may therefore be described as having multiple sites that collectively secure a given entity to the magnetic nanoparticles.

To provide the desired anchoring effect, the anchoring polymer segment will have a binding affinity toward the magnetic nanoparticles. The specific mode by which an anchoring segment binds to the particulate material is not particularly important, for example it might be by way of electrostatic forces, hydrogen bonding, ionic charge, Van der Waals forces, or any combination thereof. A particular advantage provided by the anchoring polymer segment is that it can provide multiple sites for binding interactions with the nanoparticles. Thus, even where a given binding site only provides a relatively weak interaction with the magnetic nanoparticles, the presence of multiples of such sites within the segment enables it as a whole to bind securely with the magnetic nanoparticles.

The anchoring polymer segment required will generally be dictated by the nature of the magnetic nanoparticles to which it is to bind. Those skilled in the art will be able to select an appropriate anchoring polymer segment to bind with the surface of given magnetic nanoparticles.

Those skilled in the art will appreciate the variety of polymers that may be employed as the anchoring polymer segment, as to the monomers that may be polymerised to form such polymers. For example, suitable polymers include, but are not limited to, polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, the corresponding poly-3-(diethylamino) ethyl and propyl acrylates and methacrylates, hydrophobic acrylate and methacrylate polymers, polydimethylaminoethylmethacrylate, and copolymers thereof. Thus, suitable monomers that may be used to form the anchoring polymer segment include, but are not limited to, acrylic acid, methacrylic acid, itaconic acid, p-styrene carboxylic acids, p-styrene sulfonic acids, vinyl sulfonic acid, vinyl phosphonic acid, monoacryloxyethyl phosphate, 2-(methylacryloyloxy) ethyl phosphate, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, the corresponding 3-(diethylamino) ethyl and propyl acrylates and methacrylates, styrene, hydrophobic acrylate and methacrylate monomers, dimethylaminoethylmethacrylate, and combinations thereof.

The anchoring polymer segment may comprise from about 1 to about 20 phosphonate groups, such as 1 phosphonate group, 2 phosphonate groups, 3 phosphonate groups, 4 phosphonate groups, 5 phosphonate groups, 6 phosphonate groups, 7 phosphonate groups, 8 phosphonate groups, 9 phosphonate groups or 10 phosphonate groups, 11 phosphonate groups, 12 phosphonate groups, 13 phosphonate groups, 14 phosphonate groups, 15 phosphonate groups, 16 phosphonate groups, 17 phosphonate groups, 18 phosphonate groups, 19 phosphonate groups or 20 phosphonate groups. In some embodiments, the anchoring polymer segment may comprise more than 20 phosphonate groups. In certain embodiments, the anchoring polymer segment comprises 5 phosphonate groups.

The anchoring polymer segment may be formed by the polymerisation of one type of monomer or a combination of two or more different monomers. Accordingly, the anchoring polymer segment may be a homopolymer segment or a copolymer segment.

Although there is no particular limitation on the number of polymerised monomer units that collectively form the anchoring polymer segment, in some embodiments of the invention it may be desirable that it has a relatively low number average molecular weight. The anchoring polymer segment may comprise less than about 50, or less than about 40, or less than about 30, or from about 5 to about 25, or from about 5 to about 15 polymerised monomer residue units (that make up the overall segment).

In one embodiment, the anchoring polymer segment comprises 1 to about 30 polymerised monomer residue units.

In one embodiment, the anchoring polymer segment is made up of polymerised residues of one or more ethylenically unsaturated monomers.

In some embodiments it will be appreciated the anchoring polymer segment is covalently coupled to either a steric stabilising polymer segment or a linking polymer segment so as to form the polymeric steric stabiliser, polymeric targeting moiety or polymeric luminescent moiety.

The polymeric targeting moiety and luminescent targeting moiety (when used) may comprise a linking polymer segment. As noted, that linking polymer segment is covalently coupled to an anchoring polymer segment. By being a "linking" polymer segment is meant that it is a polymer chain that links or joins the anchoring polymer segment to either targeting or luminescent groups. Accordingly, those targeting or luminescent groups will generally be covalently coupled to the linking polymer segment. The linking polymer segment also serves to separate and move the targeting or luminescent groups away from the magnetic nanoparticles to thereby make them more functional, for example in the case of targeting groups more available to receptors on targeted cells.

The linking polymer segment may comprise or consist of polyacrylamide (PA), polyvinyl alcohol (PVA), polyethylene oxide (PEO), polypropylene oxide (PPO), polyalkylene oxide, polyoxamers, polyhydroxyethylacrylate, poly-N-isopropylacrylamide, polydimethylamino-ethylmethacrylate, polyvinyl pyrrolidone (PVP), polyacrylicacid (PAA), polyacrylate, polymethacrylate, polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of any of the aforementioned.

In certain embodiments, the linking polymer segment has less than about 100 polymerised monomer residue units and, in certain embodiments, has from about 50 to about 80 polymerised monomer residue units, such as about 70 polymerised monomer residue units that make up the overall polymer segment.

In one embodiment, the linking polymer segment consists of polyacrylamide.

In another embodiment, the linking polymer segment comprises or is made up of about 10 to about 100 polymerised monomer residue units.

In a further embodiment of the linking polymer segment of one or both of the polymeric targeting moiety and luminescent targeting moiety has more polymerised monomer residue units than the steric stabilising polymer segment. For example, the linking polymer segment may have at least 2, or at least 4, at least 6, or at least 8, for at least 10, or at least 12, or at least 14, or at least 16, or at least 18, or at least 20 more polymerised monomer residue units than the steric stabilising polymer segment. The linking polymer segment may have from about 5 to about 70, or about 5 to about 60, or about 5 to about 40, or about 5 to about 20, or about 40 to about 70, or about 50 to about 70 more polymerised monomer residue units than the steric stabilising polymer segment.

Without wishing to be limited by theory, it is believed providing the linking polymer segment with more polymerised monomer residue units than the steric stabilising polymer segment plays a role in generating a surface environment that is less prone to protein adsorption and subsequent cell uptake in macrophages. That in turn is believed to improve retention of the coated nanoparticles in sentinel nodes.

The polymeric targeting moiety and polymeric luminescent moiety each comprise one or more targeting groups or one or more luminescent groups, respectively. Those targeting and luminescent groups will generally be covalently coupled to the linking polymer segment of the respective moieties.

The one or more targeting groups will be capable of selectively targeting lymph nodes or cancer cells in the subject upon administration of the coated nanoparticles. Suitable targeting groups include monosaccharide groups, antibodies, antibody fragments, ligands, and inhibitors. Interstitium is composed mainly of entangled collagen fibres and glycosaminoglycans, and the major glycosaminoglycan is negatively charged hyaluronic acid. Therefore, coated nanoparticles carrying a neutral or net negative charge are expected to promote the interstitial transfer of the nanoparticles. Also, the coated nanoparticles move through the interstitium via water channels. Therefore, surrounding the nanoparticles with hydrophilic materials may lead to more efficient movement than covering them with hydrophobic materials.

Examples of suitable targeting monosaccharide groups include, but are not limited to, mannose and glucose. Examples of suitable targeting antibodies and inhibitors include, but are not limited to Prostate Specific Membrane Antigen (PSMA) targeted antibodies, antibody fragments or inhibitors such as Lys-Urea-Glu and J591, CD147 targets (head and neck specific), Epidermal Growth Factor Receptor (EGFR) antibodies or inhibitors (used for targeting many solid tumour cancers), Cetuximab (used for the targeting of solid tumours including colorectal cancer, non-small cell lung cancer and head and neck cancer), and Panitumumab (formerly ABX-EGF, used for the targeting of solid tumours including colorectal, non-small cell lung, and head and neck cancer).

In one embodiment, the one or more targeting groups are selected from a monosaccharide group for selectively targeting monosaccharide receptors, and antibodies, antibody fragments and inhibitors for selectively targeting Prostate Specific Membrane Antigen (PSMA).

In another embodiment, the one or more targeting groups are selected from a monosaccharide group for selectively targeting monosaccharide receptors, and antibody fragments and inhibitors for selectively targeting Prostate Specific Membrane Antigen (PSMA).

In yet another embodiment, the one or more targeting groups are selected from a monosaccharide group for selectively targeting monosaccharide receptors, and inhibitors for selectively targeting Prostate Specific Membrane Antigen (PSMA).

In a further embodiment, the one or more targeting groups is an inhibitor and that inhibitor is Lys-Urea-Glu.

In a another embodiment, the one or more targeting groups is a monosaccharide selected from mannose and glucose.

The one or more luminescent group can be any chemical entity that emits electromagnetic radiation or acoustic energy at a desired wavelength following some form of stimulation. The luminescent group may be chemiluminescent (eg, bioluminescent), electroluminescent, photoluminescent, radioluminescent or thermoluminescent. In certain embodiments, the luminescent group is a photoluminescent group that emits light at a specific wavelength following absorption of photons. The photoluminescent group may be fluorescent or phosphorescent.

In certain embodiments, the luminescent group is a fluorescent group belonging to the group of cyanine dyes. Suitable fluorescent groups include indocyanine green (ICG; sodium 4-[2-[(1E,3E,5E,7Z)-7-[1,1-dimethyl-3-(4-sulfonatobutyl)benzo[e]indol-2-ylidene]hepta-1,3,5-trienyl]-1,1-dimethylbenzo[e]indol-3-ium-3-yl]butane-1-sulfonate), IR dyes such as IRdye 800 and sulfocyanine dyes such as sulfo-Cy3, sulfo-Cy5, and sulfo-Cy7. Suitable dyes are available commercially, for example, from Lumiprobe Corporation, Hunt Valley, Maryland, USA.

In one embodiment, the luminescent group is selected from indocyanine green, sulfo-Cy3, sulfo-Cy5, and sulfo-Cy7.

In some embodiments, the polymer composition further comprises (iv) a luminescent group(s) that is not covalently coupled to a polymer. By a luminescent group not being covalently coupled to a polymer is meant the luminescent group does not form part of the polymeric luminescent moiety and is present in the polymer composition as a luminescent group per se. Suitable luminescent groups for that purpose include those herein described.

In certain embodiments, the polymer composition coating comprises at least one polymeric steric stabiliser and at least one polymeric targeting moiety. In other embodiments, the polymer composition coating comprises at least one polymeric steric stabiliser and at least one polymeric luminescent moiety. In other embodiments, the polymer composition coating comprises at least one polymeric steric stabiliser, at least one polymeric targeting moiety and at least one polymeric luminescent moiety.

An example of a therapeutic use of the coated nanoparticles or compositions comprising them is sensitising radiotherapy.

Examples of diagnostic uses of the coated nanoparticles or compositions comprising them include in magnetic resonance imaging, in cancer surgery and in visualising lymph node metastases.

The present invention provides a composition suitable for administration to a subject for use in diagnostic and/or therapeutic imaging application, the composition comprising the pharmacologically acceptable coated nanoparticles described herein dispersed in a pharmacologically acceptable liquid carrier.

The coated nanoparticles and the composition comprising them can be used in conjunction with in vivo imaging techniques including, but not limited to, ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

In one application, the coated nanoparticles and composition comprising them allow for detection of tissue such as lymph nodes that have taken up the coated nanoparticles upon injection of the nanoparticles into a subject. That can be used to identify tissue that could be affected by certain forms of cancer. The sentinel lymph node is the hypothetical first lymph node or group of nodes draining a cancer. It is postulated that the sentinel lymph nodes are the target organs primarily reached by metastasizing cancer cells from tumours. The coated nanoparticles and composition comprising them can therefore be used for detection of sentinel lymph nodes and used as part of a sentinel node procedure comprising the identification, removal and analysis of the sentinel lymph nodes of a particular tumour.

Thus, there is also provided use of the coated nanoparticles or composition comprising them for in vivo imaging.

There is further provided use of the coated nanoparticles or compositions comprising them for detection of sentinel lymph nodes.

The in vivo imaging techniques enable at least location detection or visualisation of the coated nanoparticles in a subject and in turn therefore enable the detection or identification of sentinel lymph nodes and/or tissue effected by cancer.

In one embodiment, the in vivo imaging is selected from the group consisting of ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

The present invention therefore also provides a method for the detecting cancer in a subject, the method comprising: administering the pharmacologically acceptable magnetic nanoparticles or the composition according to the invention to the subject; and detecting the magnetic nanoparticles, wherein the localisation of magnetic nanoparticles indicates the presence of tissue affected by cancer in the subject.

The present invention further provides a method for the treatment of a subject with cancer, the method comprising: administering the pharmacologically acceptable magnetic nanoparticles or the composition according to the invention to the subject; detecting the magnetic particles: identifying the subject as having cancer, wherein the localisation of magnetic particles indicates the presence of tissue affected by cancer in the subject; and treating a subject identified as having cancer in (iii) with a treatment for cancer.

In one embodiment, polymeric steric stabiliser may be described as having the general formula $Z^1$-$A^1$-$S^1$—[$S^2$]—[Y], wherein $A^1$ comprises an anchoring polymer segment comprising one or more binding group capable of binding to the metal/magnetic core; $S^1$ comprises a first steric stabilising polymer segment capable of minimising aggregation of the coated nanoparticles in a liquid; $S^2$ is a second steric stabilising polymer segment and employed to enhance a desirable biological characteristic; $Z^1$ and Y are polymer end groups; and [ ] designates that the group may or may not be present.

In one embodiment, the polymeric targeting moiety may be described as having the general formula $Z^2$-$A^2$-$L^1$-T, wherein $A^2$ comprises an anchoring polymer segment comprising one or more binding group capable of binding to the metal/magnetic core; $L^1$ comprises a linking polymer segment employed to move T away from the metal/magnetic core; T is one or more targeting group capable of selectively targeting lymph nodes or cancer cells in the subject upon administration of the coated nanoparticles; and $Z^2$ is a polymer end group.

In one embodiment, the polymeric luminescent moiety may be described as having the general formula -$A^3$-$L^2$-F, wherein $A^3$ comprises an anchoring polymer segment comprising one or more binding group capable of binding to the metal/magnetic core; $L^2$ comprises a linking polymer segment employed to move F away from the metal/magnetic core; and F is one or more luminescent group capable of emitting light for in vivo visualisation of the coated nanoparticles.

As used herein, polymers have the formula —X— where "-" designates a bond between two groups such that the two groups are operably linked. As used herein, the term "operably linked" refers to the linkage of a first element to a second element such that the first element and second element are placed in a functional relationship. The bond may be a direct bond between two groups or polymer segments. Alternatively, a designated bond may be an indirect bond between two groups or polymer segments and there may be additional groups or polymer segments between the two designated groups or segments. For example, a polymer segment having the formula "-$A^1$-S—" includes within its scope polymer segments having the formula "-$A^1$-S— and also polymer segments having the formula -$A^1$-B—S— where B can be any group of polymer segment that does not substantially affect the properties of the polymer or polymer segment.

The polymeric steric stabiliser, polymeric targeting moiety and polymeric luminescent moiety are separate polymer entities such that the polymer composition coating comprises a mixture of each separate polymer moiety.

The steric stabilising polymer $S^1$ and/or $S^2$ segment may contain a first polymer segment with certain characteristics to improve robustness of the polymer, and a second polymer segment to improve biological characteristics of the polymer. For example, the second polymer segment may increase blood circulation half-life.

The linking polymer segments $L^1$ and/or $L^2$ are preferably polymer segments to improve the robustness of the polymer segment, and are different to the steric stabilising polymer segment.

The polymer composition coating may comprise at least one polymeric steric stabiliser having the general formula $Z^1$-$A^1$-$S^1$—[$S^2$]—[Y], wherein $A^1$ comprises an anchoring polymer segment comprising one or more binding group capable of binding to the metal core; $S^1$ comprises a steric stabilising polymer segment optimised for minimising aggregation of coated nanoparticles in solution; $S^2$ comprises a steric stabilising polymer segment optimised for a biological interaction such as increased blood circulation half-life; $Z^1$ and Y are polymer end groups; and [ ] designates that the group may or may not be present.

The anchoring polymer segment (A') comprises one or more binding group capable of binding to the metal/magnetic core. The one or more binding group may be part of the polymer backbone or they may be pendant groups that are attached to side chains of the polymer backbone. The binding group can be any element or molecule with a binding affinity for the material in the metal/magnetic core. For example, the binding group can be any element or molecule with a binding affinity for iron or iron oxide. Suitable binding groups that can be used include groups comprising one or more phosphorous (P) atom, groups comprising one or more oxygen (O) atom, groups comprising one or more sulfur (S) atom, groups comprising one or more nitrogen (N) atom, and groups comprising any two or more of the aforementioned atoms. Particularly suitable binding groups that can be used include phosphate groups, phosphonate groups, dimercaptosuccinic acid (DMSA) groups, sulfate groups, sulfonate groups, catechol groups, carboxyl groups, amine groups, and silane groups.

Suitable phosphate groups have the general formula —OP(O)(OH)$_2$.

Suitable phosphonate groups have the general formula —P(O)(OH)$_2$.

Suitable dimercaptosuccinic acid (DMSA) groups have the general formula:

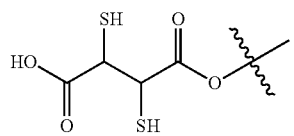

Suitable sulfate groups have the general formula —OS(O)$_2$OH.

Suitable sulfonate groups have the general formula —S(O)$_2$OH.

Suitable catechol groups have the general formula:

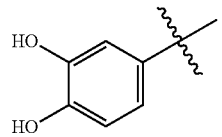

Suitable carboxyl groups have the general formula —C(O)OH.

Suitable amine groups have the general formula —NH$_2$.

Suitable silane groups have the general formula —Si(OH)$_3$.

The anchoring polymer segment (A$^1$) may comprise two or more different binding groups.

The anchoring polymer segment (A$^1$) may comprise more than one binding group and it is expected that the binding affinity of the anchoring polymer segment (A$^1$) for the metal/magnetic core may increase with the number of binding groups present. Ideally, the anchoring polymer segment (A$^1$) provides multiple sites for binding interactions with the metal/magnetic core. The presence of multiple binding sites within the anchoring polymer segment (A$^1$) enables it as a whole to bind securely with the metal/magnetic core. By way of a non-limiting example, the present inventors have shown that phosphonate groups bind to iron nanoparticles. In the case of phosphonate binding groups, each anchoring polymer segment (A$^1$) may contain from about 1 to about 20 phosphonate groups, such as 1 phosphonate group, 2 phosphonate groups, 3 phosphonate groups, 4 phosphonate groups, 5 phosphonate groups, 6 phosphonate groups, 7 phosphonate groups, 8 phosphonate groups, 9 phosphonate groups or 10 phosphonate groups, 11 phosphonate groups, 12 phosphonate groups, 13 phosphonate groups, 14 phosphonate groups, 15 phosphonate groups, 16 phosphonate groups, 17 phosphonate groups, 18 phosphonate groups, 19 phosphonate groups or 20 phosphonate groups. In some embodiments, the anchoring polymer segment (A$^1$) may contain more than 20 phosphonate groups. In certain embodiments, each anchoring polymer segment (A$^1$) contains 5 phosphonate groups.

The anchoring polymer segment (A$^1$) has a polymer backbone. The anchoring polymer segment (A$^1$) may be derived from one or more ethylenically unsaturated monomer. Optionally, two or more different polymers may be used as the anchoring polymer segment (A$^1$ and A$^{1\prime}$) in the composition.

The anchoring polymer segment (A$^1$) may have the general formula I:

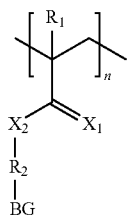

(I)

wherein:

R$^1$ is selected from the group consisting of H, halogen, optionally substituted C$_1$-C$_6$ alkyl, and optionally substituted aryl;

X$_1$ and X$_2$ are each independently selected from the group consisting of O, S, and N;

R$_2$ is a bond or is a group selected from optionally substituted C$_1$-C$_6$ alkyl, and optionally substituted aryl;

BG is a binding group as defined herein; and n is an integer number selected from the group consisting of 1, 2, 3, 4, 5, 6, 7, 8, 9, 10, 11, 12, 13, 14, 15, 16, 17, 18, 19, and 20.

In certain embodiments, R$_1$ is optionally substituted C$_1$-C$_6$ alkyl. In certain specific embodiments, R$_1$ is CH$_3$.

In certain embodiments, X$_1$ is O.

In certain embodiments, X$_2$ is O.

In certain embodiments, R$_2$ is optionally substituted C$_1$-C$_6$ alkyl. In certain specific embodiments, R$_2$ is —(CH$_2$)$_2$—.

In certain embodiments, BG is a phosphonate binding group. In certain specific embodiments, BG is —P(O)(OH)$_2$.

In certain embodiments, n is 5.

From the foregoing, it will be evident that in certain embodiments, the anchoring polymer segment (A') has the formula:

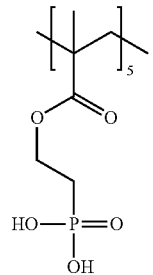

The first steric stabilising polymer segment (S$^1$) is a polymer segment that is capable of minimising aggregation of coated nanoparticles in solution. Without intending to be bound by any one specific theory on the mode of action of the first steric stabilising polymer segment (S$^1$), it is expected that the first steric stabilising polymer segment (S$^1$) interacts with both the metal/magnetic core material and the surrounding liquid environment and helps maintain the particulate material in a dispersed state as a result of electrostatic and/or steric repulsion forces.

The first steric stabilising polymer segment (S$^1$) has a polymer backbone. The chemical functionality of the first steric stabilising polymer segment (S$^1$) is not especially important and, for example, the first steric stabilising polymer segment (S$^1$) may be a polyacrylamide (PA), polyvinyl alcohol (PVA), polyethylene oxide (PEO), polypropylene oxide (PPO), polyalkylene oxide, polyoxamers, polyhydroxyethylacrylate, poly-N-isopropylacrylamide, polydimethylamino-ethylmethacrylate, polyvinyl pyrrolidone (PVP), polyacrylicacid (PAA), polyacrylate, polymethacrylate, polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of any of the aforementioned.

As discussed, a function of the first steric stabilising polymer segment (S$^1$) is to help maintain the magnetic nanoparticles in a dispersed state as a result of electrostatic and/or steric repulsion forces. For this reason, the length of the sterically stabilising polymer segment (S$^1$) needs to be sufficient to provide the required steric repulsion forces. It also needs to be taken into account that the anchoring polymer segment ($A^1$) and, if present, the second steric stabilising polymer segment ($S^2$) also have a length and/or functionality that contributes to the required electrostatic and/or steric repulsion forces. For this reason, in certain embodiments, the first steric stabilising polymer segment ($S^1$) has less than about 70 polymerised monomer residue units and, in certain embodiments, has from about 40 to about 60 polymerised monomer residue units, such as about 50 polymerised monomer residue units that make up the overall polymer segment. In certain embodiments, the first steric stabilising polymer segment ($S^1$) has a molecular weight of from about 1,000 g/mol to about 10,000 g/mol.

In certain embodiments, the first steric stabilising polymer segment ($S^1$) has the general formula II:

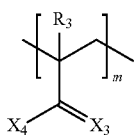

(II)

wherein:

$R_3$ is selected from the group consisting of H, halogen, optionally substituted $C_1$-$C_6$ alkyl, and optionally substituted aryl;

$X_3$ and $X_4$ are each independently selected from the group consisting of O, S, and N; and m is an integer number from 40 to 70.

In certain embodiments, $R_3$ is H.

In certain embodiments, $X_3$ is O.

In certain embodiments, $X_4$ is $NR_4R_5$, wherein $R_4$ and $R_5$ are each independently selected from the group consisting of H, optionally substituted alkyl, and optionally substituted aryl.

In certain embodiments, m is 50.

From the foregoing, it will be evident that in certain embodiments the first steric stabilising polymer segment ($S^1$) has the formula:

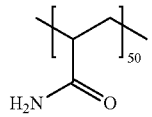

The second steric stabilising polymer segment ($S^2$) comprises a polymer backbone. The second steric stabilising polymer segment ($S^2$) may form a relatively hydrophilic surface on the coated nanoparticles which means that the surface of the coated nanoparticles can be wetted with an aqueous solution and preferentially optimises in-vivo interactions with biological material, such as minimising interactions where the blood circulation half-life needs to be maximised.

The second steric stabilising polymer segment ($S^2$) may comprise a polymer chain selected from polyalkylene oxide polymers such as polyethylene glycol, polypropylene glycol, poloxamers and poloxamines (block copolymers of polyoxyethylene and polyoxypropylene), and alkyl end capped derivatives thereof. The second stabilising polymer segment ($S^2$) may also comprise a relatively hydrophobic polymer backbone having pendant hydrophilic groups. In all cases, the polymer segment ($S^2$) may comprise one or more hydrophilic pendant group selected from the group consisting of —$CO_2H$, —$CO_2RN$, —$SO_3H$, —$OSO_3H$, —SORN, —$SO_2RN$, —$OP(OH)_2$, —$P(OH)_2$, —$PO(OH)_2$, —OH, —ORN, —$(OCH_2$—$CHR)_w$—OH, —$CONH_2$, CONHR', CONR'R", —NR'R", —N+R'R"R''', where R is selected from $C_1$-$C_6$ alkyl, w is 1 to 10, R', R" and R''' are independently selected from alkyl and aryl which are optionally substituted with one or more hydrophilic substituents selected from —$CO_2H$, —$SO_3H$, —$OSO_3H$, —OH, —$(COCH_2CHR)_w$—OH, —$CONH_2$, —SOR and $SO_2R$, and salts thereof, and R and w are as defined above.

In certain embodiments, the second stabilising polymer segment ($S^2$) comprises a polyalkylene oxide polymer. The polyalkylene oxide polymer may be selected from polyethylene glycol, polypropylene glycol and derivatives thereof. The polyalkylene oxide polymer may be end capped with an alkyl group. The alkyl group may be a $C_1$ to $C_6$ alkyl group, such as a methyl group, an ethyl group, a propyl group or an isopropyl group.

In certain embodiments, the second steric stabilising polymer segment ($S^2$) has the general formula III:

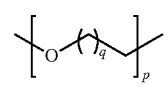

III wherein p is an integer number from 10 to 30 and q is an integer number selected from 1, 2 and 3.

In certain embodiments, q is 1. In other certain embodiments, q is 2.

In certain embodiments, p is an integer number from 15 to 25, such as 15, 16, 17, 18, 19, 20, 21, 22, 23, 24 or 25.

From the foregoing, it will be evident that in certain embodiments, the polymeric steric stabiliser is a polyphosphate/polyacrylamide/PEO polymer. The polyphosphate/polyacrylamide/PEO polymer in certain embodiments has the formula:

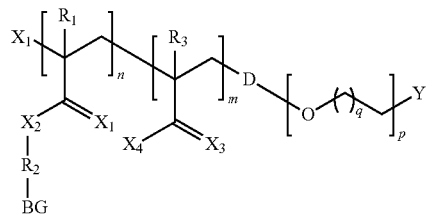

wherein $X_1$, $X_2$, $X_3$, $X_4$, $R_1$, $R_2$, $R_3$, BG, n, m, p, q are as previously defined herein, $Z^1$ is a polymer chain end group, such as a trithiocarbonate derived from a RAFT agent, Y is a polymer end group, such as an alkyl group, and D is a linker group, such as an -alkyl-C(O)— group.

In certain specific embodiments, the polymeric steric stabiliser has the formula:

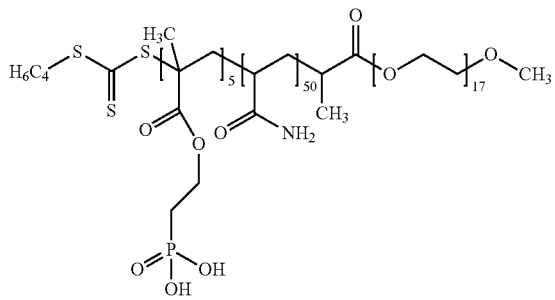

In certain embodiments, the polymeric steric stabiliser having the general formula $Z^1$-$A^1$-$S^1$—[$S^2$]—[Y] is formed by reversible addition fragmentation chain transfer (RAFT) polymerisation. In these embodiments, the $Z^1$ and Y polymer end groups may be derived from the particular RAFT agent used. For example, the $Z^1$ group may be a trithiocarbonate group derived from the RAFT agent. The trithiocarbonate group may be an alkyl trithiocarbonate group, such as a methyl trithiocarbonate group.

In addition to the polymeric steric stabiliser, the polymer composition coating may also comprise a polymeric targeting moiety having the general formula $Z^2$-$A^2$-$L^1$-T. The polymeric targeting moiety targets lymph nodes or cancer cells in a subject to whom the coated nanoparticles are administered.

The anchoring polymer segment ($A^2$) has a polymer backbone. The anchoring polymer segment ($A^2$) may be derived from one or more ethylenically unsaturated monomers.

The anchoring polymer segment ($A^2$) may have the general formula IV:

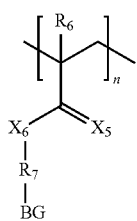 (IV)

wherein:

$R_6$ is selected from the group consisting of H, halogen, optionally substituted $C_1$-$C_6$ alkyl, and optionally substituted aryl;

$X_5$ and $X_6$ are each independently selected from the group consisting of O, S, and N;

$R_7$ is a bond or is a group selected from optionally substituted $C_1$-$C_6$ alkyl, and optionally substituted aryl;

BG is a binding group as defined herein; and n is an integer number selected from the group consisting of 1, 2, 3, 4, 5, 6, 7, 8, 9, and 10.

In certain embodiments, $R_6$ is optionally substituted $C_1$-$C_6$ alkyl. In certain specific embodiments, $R_6$ is $CH_3$.

In certain embodiments, $X_5$ is O.

In certain embodiments, $X_6$ is O.

In certain embodiments, $R_7$ is optionally substituted $C_1$-$C_6$ alkyl. In certain specific embodiments, R, is —$(CH_2)_2$—.

In certain embodiments, BG is a phosphonate binding group. In certain specific embodiments, BG is —$P(O)(OH)_2$.

In certain embodiments, n is 5.

From the foregoing, it will be evident that in certain embodiments, the anchoring polymer segment ($A^2$) has the formula:

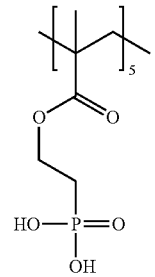

The linking polymer segment (L') has a polymer backbone. The linking polymer segment ($L^1$) may be a polyacrylamide (PA), polyvinyl alcohol (PVA), polyethylene oxide (PEO), polypropylene oxide (PPO), polyalkylene oxide, polyoxamers, polyhydroxyethylacrylate, poly-N-isopropylacrylamide, polydimethylamino-ethylmethacrylate, polyvinyl pyrrolidone (PVP), polyacrylicacid (PAA), polyacrylate, polymethacrylate, polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of any of the aforementioned.

In certain embodiments, the linking polymer segment ($L^1$) has less than about 100 polymerised monomer residue units and, in certain embodiments, has from about 50 to about 80 polymerised monomer residue units, such as about 70 polymerised monomer residue units that make up the overall polymer segment. The linking polymer moves the targeting group (T) away for the metal core to make it available to receptors on targeted cells.

In certain embodiments, the linking polymer segment ($L^1$) has the general formula V:

 (V)

wherein:

$R_s$ is selected from the group consisting of H, halogen, optionally substituted $C_1$-$C_6$ alkyl, and optionally substituted aryl;

$X_7$ and $X_8$ are each independently selected from the group consisting of O, S, and N; and m is an integer number from 50 to 80.

In certain embodiments, $R_8$ is H.

In certain embodiments, $X_7$ is O.

In certain embodiments, $X_8$ is $NR_9R_{10}$, wherein $R_9$ and $R_{10}$ are each independently selected from the group consisting of H, optionally substituted alkyl, and optionally substituted aryl.

In certain embodiments, m is 70.

From the foregoing, it will be evident that in certain embodiments the linking polymer segment ($L^1$) has the formula:

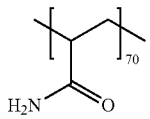

T is one or more targeting group capable of selectively targeting lymph nodes or cancer cells in the subject upon administration of the coated nanoparticles. Suitable targeting groups include monosaccharide groups, Prostate Specific Membrane Antigen (PSMA) targeting groups, such as antibodies, antibody fragments, ligands, and inhibitors. Interstitium is composed mainly of entangled collagen fibres and glycosaminoglycans, and the major glycosaminoglycan is negatively charged hyaluronic acid. Therefore, coated nanoparticles carrying a neutral or net negative charge are expected to promote the interstitial transfer of the nanoparticles. Also, the coated nanoparticles move through the interstitium via water channels. Therefore, surrounding the nanoparticles with hydrophilic materials may lead to more efficient movement than covering them with hydrophobic materials. Examples of suitable monosaccharide groups include, but are not limited to, mannose and glucose. Examples of suitable antibodies and inhibitors include, but are not limited to Prostate Specific Membrane Antigen (PSMA) targeted antibodies, antibody fragments or inhibitors such as Lys-Urea-Glu and J591, CD147 targets (head and neck specific), Epidermal Growth Factor Receptor (EGFR) antibodies or inhibitors (used for targeting many solid tumour cancers), Cetuximab (used for the targeting of solid tumours including colorectal cancer, non-small cell lung cancer and head and neck cancer), and Panitumumab (formerly ABX-EGF, used for the targeting of solid tumours including colorectal, non-small cell lung, and head and neck cancer). Examples of suitable PSMA targeting groups include, but are not limited to PSMA targeted antibodies, PSMA targeted antibody fragments and inhibitors (e.g., Lys-Urea-Glu).

The polymer composition coating may contain the polymeric steric stabiliser and the polymeric targeting moiety in any suitable amounts. For example, the polymer composition coating may contain 10%-90% (wt/wt) of the polymeric steric stabiliser and 90%-10% (wt/wt) of the polymeric targeting moiety. In certain embodiments, the polymer composition coating contains 10% (wt/wt) of the polymeric steric stabiliser and 90% (wt/wt) of the polymeric targeting moiety, 15% (wt/wt) of the polymeric steric stabiliser and 85% (wt/wt) of the polymeric targeting moiety, 20% (wt/wt) of the polymeric steric stabiliser and 80% (wt/wt) of the polymeric targeting moiety, 25% (wt/wt) of the polymeric steric stabiliser and 75% (wt/wt) of the polymeric targeting moiety, 30% (wt/wt) of the polymeric steric stabiliser and 70% (wt/wt) of the polymeric targeting moiety, 35% (wt/wt) of the polymeric steric stabiliser and 65% (wt/wt) of the polymeric targeting moiety, 40% (wt/wt) of the polymeric steric stabiliser and 60% (wt/wt) of the polymeric targeting moiety, 45% (wt/wt) of the polymeric steric stabiliser and 55% (wt/wt) of the polymeric targeting moiety, 50% (wt/wt) of the polymeric steric stabiliser and 50% (wt/wt) of the polymeric targeting moiety, 55% (wt/wt) of the polymeric steric stabiliser and 45% (wt/wt) of the polymeric targeting moiety, 60% (wt/wt) of the polymeric steric stabiliser and 40% (wt/wt) of the polymeric targeting moiety, 65% (wt/wt) of the polymeric steric stabiliser and 35% (wt/wt) of the polymeric targeting moiety, 70% (wt/wt) of the polymeric steric stabiliser and 30% (wt/wt) of the polymeric targeting moiety, 75% (wt/wt) of the polymeric steric stabiliser and 25% (wt/wt) of the polymeric targeting moiety, 80% (wt/wt) of the polymeric steric stabiliser and 20% (wt/wt) of the polymeric targeting moiety, 85% (wt/wt) of the polymeric steric stabiliser and 15% (wt/wt) of the polymeric targeting moiety or 90% (wt/wt) of the polymeric steric stabiliser and 10% (wt/wt) of the polymeric targeting moiety. In certain specific embodiments, the polymer composition coating contains 70% (wt/wt) of the polymeric steric stabiliser and 30% (wt/wt) of the polymeric targeting moiety.

In addition to, or as an alternative to the polymeric targeting moiety, the polymer composition coating may also comprise a polymeric luminescent moiety having the general formula $-A^3-L^2-F$, wherein $A^3$ comprises an anchoring polymer segment comprising one or more binding group capable of binding to the metal/magnetic core; L comprises a linking polymer segment; and F is one or more luminescent group capable of emitting electromagnetic radiation for in vivo visualisation of the coated nanoparticles. The linking polymer segment (L) spaces the luminescent group (F) away from the metal/magnetic core to minimise absorption of emitted light by the metal core.

The anchoring polymer segment ($A^3$) may have the general formula VI:

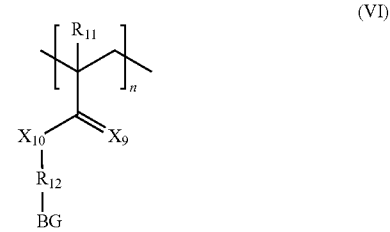

(VI)

wherein:

$R_{11}$ is selected from the group consisting of H, halogen, optionally substituted $C_1$-$C_6$ alkyl, and optionally substituted aryl;

$X_9$ and $X_{10}$ are each independently selected from the group consisting of O, S, and N;

$R_{12}$ is a bond or is a group selected from optionally substituted $C_1$-$C_6$ alkyl, and optionally substituted aryl;

BG is a binding group as defined herein; and n is an integer number selected from the group consisting of 1, 2, 3, 4, 5, 6, 7, 8, 9, and 10.

In certain embodiments, $R_{11}$ is optionally substituted $C_1$-$C_6$ alkyl. In certain specific embodiments, $R_1$ is $CH_3$.

In certain embodiments, $X_9$ is O.

In certain embodiments, $X_{10}$ is O.

In certain embodiments, $R_{12}$ is optionally substituted $C_1$-$C_6$ alkyl. In certain specific embodiments, $R_2$ is $—(CH_2)_2—$.

In certain embodiments, BG is a phosphonate binding group. In certain specific embodiments, BG is $—P(O)(OH)_2$.

In certain embodiments, n is 5.

From the foregoing, it will be evident that in certain embodiments, the anchoring polymer segment ($A^3$) has the formula:

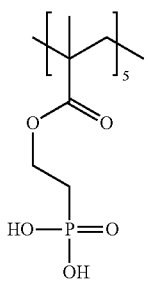

The linking polymer segment (L²) has a polymer backbone. The linking polymer segment (L²) may be a polyacrylamide (PA), polyvinyl alcohol (PVA), polyethylene oxide (PEO), polypropylene oxide (PPO), polyalkylene oxide, polyoxamers, polyhydroxyethylacrylate, poly-N-isopropylacrylamide, polydimethylamino-ethylmethacrylate, polyvinyl pyrrolidone (PVP), polyacrylicacid (PAA), polyacrylate, polymethacrylate, polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of any of the aforementioned.

In certain embodiments, the linking polymer segment (L²) has less than about 100 polymerised monomer residue units and, in certain embodiments, has from about 50 to about 80 polymerised monomer residue units, such as about 70 polymerised monomer residue units that make up the overall polymer segment.

In certain embodiments, the linking polymer segment (L²) has the general formula VII:

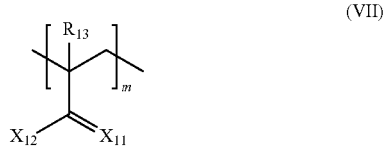

(VII)

wherein:

$R_{13}$ is selected from the group consisting of H, halogen, optionally substituted $C_1$-$C_6$ alkyl, and optionally substituted aryl;

$X_{11}$ and $X_{12}$ are each independently selected from the group consisting of O, S, and N; and m is an integer number from 50 to 80.

In certain embodiments, $R_{13}$ is H.
In certain embodiments, $X_{11}$ is O.
In certain embodiments, $X_{12}$ is $NR_{14}R_{15}$, wherein $R_{14}$ and $R_{15}$ are each independently selected from the group consisting of H, optionally substituted alkyl, and optionally substituted aryl.

In certain embodiments, m is 70.

From the foregoing, it will be evident that in certain embodiments the linking polymer segment (L²) has the formula:

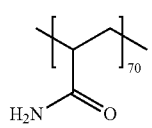

The polymeric luminescent moiety comprises one or more luminescent group (F) that are capable of emitting electromagnetic radiation or acoustic energy for in vivo visualisation of the coated nanoparticles. The luminescent groups (F) allow for the in vivo visualisation of the coated nanoparticles in real time.

The luminescent group (F) can be any chemical entity that emits electromagnetic radiation or acoustic energy at a desired wavelength following some form of stimulation. The luminescent group (F) may be chemiluminescent (eg, bioluminescent), electroluminescent, photoluminescent, radioluminescent or thermoluminescent. In certain embodiments, the luminescent group (F) is a photoluminescent group that emits light at a specific wavelength following absorption of photons. The photoluminescent group may be fluorescent or phosphorescent.

In certain embodiments, the luminescent group (F) is a fluorescent group belonging to the group of cyanine dyes. Suitable fluorescent groups include indocyanine green (ICG; sodium 4-[2-[(1E,3E,5E,7Z)-7-[1,1-dimethyl-3-(4-sulfonatobutyl)benzo[e]indol-2-ylidene]hepta-1,3,5-trienyl]-1,1-dimethylbenzo[e]indol-3-ium-3-yl]butane-1-sulfonate), IR dyes such as IRdye 800 and sulfocyanine dyes such as sulfo-Cy3, sulfo-Cy5, and sulfo-Cy7. Suitable dyes are available commercially, for example, from Lumiprobe Corporation, Hunt Valley, Maryland, USA.

The luminescent group (F) may be used in conjunction with known surgical equipment to visualise the coated nanoparticles in vivo. Any one or more of the known fluorescence or acoustic imaging techniques can be used for this purpose.

In certain embodiments, the polymeric luminescent moiety is present in the polymer composition coating in an amount of at least about 1% by weight. In certain embodiments, the polymeric luminescent moiety is present in the polymer composition coating in an amount of from about 1% by weight to about 90% by weight, such as about 30% by weight.

Also provided herein is a composition suitable for administration to a subject. The composition find use in diagnostic and/or therapeutic imaging application. The composition comprises the coated nanoparticles described herein in a pharmacologically acceptable liquid or so called liquid carrier. The coated nanoparticles will typically be dispersed in the pharmacologically acceptable liquid.

A pharmacologically acceptable liquid may be made up of one or more different liquids. Suitable pharmacologically acceptable liquids are described in, e.g., Remington: The Science and Practice of Pharmacy, 21 st ed.; Lippincott Williams & Wilkins: Philadelphia, PA, 2005; Handbook of Pharmaceutical Excipients, 6th ed Rowe et al., Eds.; The Pharmaceutical Press and the American Pharmaceutical Association: 2009; Handbook of Pharmaceutical Additives, 3rd ed Ash and Ash Eds.; Gower Publishing Company: 2007; Pharmaceutical Preformulation and Formulation, 2nd ed Gibson Ed.; CRC Press LLC: Boca Raton, FL, 2009. Water or saline solutions and aqueous dextrose and glycerol solutions are often employed as liquid carriers, particularly for injectable compositions.

The compositions of the invention may comprise one or more pharmacologically acceptable additives known to those in the art. For example, a liquid carrier may comprise one or more additives such as wetting agents, de-foaming agents, surfactants, buffers, electrolytes, preservatives and colourings.

The particular nature of the liquid carrier and any additive therein (if present) will in part depend upon the intended application of the composition. Those skilled in the art will be able to select a suitable liquid carrier and additive (if present) for the intended application of the composition.

In compositions, such as those described herein, it is important that the coated nanoparticle dispersion remains "stable" which means that the medic nanoparticles remain dispersed throughout the liquid carrier. Ideally, the composition remains stable both before administration and after administration to a subject. The coated nanoparticles described herein will generally not aggregate when placed in the pharmacologically acceptable liquid carrier. As used herein, the term "aggregate" refers to non-amorphous cluster or collection of particles, as is determinable by electron microscopy or dynamic light scattering.

The coated nanoparticles described herein (typically as part of the compositions described herein) may be administered in, as appropriate, a diagnostic effective amount. A diagnostic effective amount is intended to include an amount which, when administered according to the desired dosing regimen, achieves a desired diagnostic effect, including diagnosing, the onset or progression of a particular condition being treated and/or assessed Suitable dosage amounts and dosing regimens to achieve that can be determined by the attending physician and may depend on the particular condition being treated or diagnosed, the severity of the condition as well the general age, health and weight of the subject.

Dosing may occur at intervals of minutes, hours, days, weeks, months or years or continuously over any one of these periods. Suitable dosages of the particulate material per se may lie within the range of about 0.1 ng per kg of body weight to 1 g per kg of body weight per dosage. The dosage may be in the range of 1 μg to 1 g per kg of body weight per dosage, such as is in the range of 1 ug to 10 mg per kg of body weight per dosage. In one embodiment, the dosage may be in the range of 1 ug to 1 mg per kg of body weight per dosage. In another embodiment, the dosage may be in the range of 1 ug to 250 ug per kg of body weight per dosage. In yet another embodiment, the dosage may be in the range of 1 ug to 100 ug per kg of body weight per dosage, such as up to 50 ug per body weight per dosage.

Compositions in accordance with the invention may be administered in a single dose or a series of doses.

Where the compositions in accordance with the invention are suitable for parenteral administration, they will generally be in the form of an aqueous or non-aqueous isotonic sterile injection solution that may contain one or more of an anti-oxidant, buffer, bactericide or solute which renders the composition isotonic with the blood of the intended subject. Such compositions may be presented in unit-dose or multi-dose scaled containers, for example, ampoules and vials.

Upon administration, compositions in accordance with the invention will often be diluted in vivo. For example, dilution can occur when the composition is administered parenterally. In that case, the liquid carrier of the composition may become so dilute in vivo that the surrounding liquid environment throughout which the coated nanoparticles is dispersed becomes more representative of an in vivo liquid (i.e. a biological liquid/fluid within the subject) than the original liquid carrier. For example, once administered parenterally, the particulate material from the composition might more aptly be described as being dispersed throughout blood rather than the original liquid carrier of the composition. Under those conditions, it may be convenient to refer to the coated nanoparticles as being dispersed throughout an in vivo liquid carrier (i.e. a biological liquid/fluid within the subject). With the exception of any compositional differences between a liquid of compositions in accordance with the invention and an in vivo liquid carrier, matters described herein relating to the liquid carrier of the composition will also generally apply to an in vivo liquid carrier.

Those skilled in the art will appreciate that the dispersed coated nanoparticles used in accordance with the invention will present a hydrodynamic diameter within a liquid carrier. The hydrodynamic diameter is the distance or size that is derived from the magnetic nanoparticles per se and at least the polymeric steric stabilisers and targeting moieties associated with the nanoparticles. The hydrodynamic diameter of the dispersed coated nanoparticles can therefore be seen to represent the diameter afforded by a combination of the magnetic nanoparticles and at least the polymeric steric stabilisers and targeting moieties. Where the dispersed coated nanoparticles do not have a symmetrical shape, the hydrodynamic diameter will be considered to be that of the largest hydrodynamic diameter presented by the dispersed coated nanoparticles.

In one embodiment, the hydrodynamic diameter of the dispersed coated nanoparticles is less than about 300 nm, less than about 250 nm, less than about 100 nm, less than about 50 nm, less than about 25 nm or less than about 15 nm.

In a further embodiment, the hydrodynamic diameter of the dispersed coated nanoparticles is about: 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

For avoidance of any doubt, reference herein to the "the hydrodynamic diameter" of the dispersed coated nanoparticles is intended to denote an average diameter (at least about 50 number %) of the dispersed coated nanoparticles. The hydrodynamic diameter of dispersed coated nanoparticles is determined herein by dynamic light scattering (DLS).

In certain embodiments, the coated nanoparticles described herein have an average hydrodynamic radius (Rh) (i.e. half of the hydrodynamic diameter) of from about 30 nm to about 150 nm, such as about 30 nm, about 40 nm, about 50 nm, about 60 nm, about 70 nm, about 80 nm, about 90 nm, about 100 nm, about 110 nm, about 120 nm, about 130 nm, about 140 nm or about 150 nm. In certain specific embodiments, the coated nanoparticles described herein have an average hydrodynamic radius (Rh) of about 90 nm. As will be well understood by the skilled person, the hydrodynamic radius (Rh) of the coated nanoparticles can also be determined by dynamic light scattering (DLS).

The size of the nanoparticles may be important in terms of their localisation in lymph nodes. One study based on dendrimers suggests that materials with diameters larger than about 9 nm tend to enter the lymphatic system, while materials with diameters smaller than about 6 nm tend to drain into the blood. Thus, coated nanoparticles with hydrodynamic diameters of 10-100 nm may be suitable for allowing efficient transfer through the interstitium and entry into the lymphatic capillaries and ultimately the lymph nodes.

Ultrasmall magnetic nanoparticles have previously been used for imaging metastases in lymph nodes. Current magnetic nanoparticle imaging techniques using MRI, PET or CT give poor sensitivity. For example, to the best of the applicant's knowledge, 11% sensitivity with PET is the current best for detecting micro-metastasis (<2 mm diameter tumour deposits). There has been some recent work by others using ultrasmall super-paramagnetic iron-oxide nanoparticles (USPIONs) (<10 nm core diameter; eg 6-8 nm and Rh of 20-30 nm) and they have shown sensitivity of 89%-98% with MRI. USPIONs enhance both T1 and T2 MRI images, while larger nanoparticles (>10 nm core diameter) enhance only T2 MRI images.

The coated nanoparticles and composition comprising them according to the invention can be used in conjunction with in vivo imaging techniques including, but not limited to, ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

In one application, the coated nanoparticles comprise a targeting group of mannose and the composition comprising them allows for detection of tissue such as lymph nodes that have taken up and retained the coated nanoparticles upon injection of the composition into a subject. That procedure can be used to identify tissue that is most likely to be affected by certain forms of cancer. The sentinel lymph node is the hypothetical first lymph node or group of nodes draining a cancer. It is postulated that the sentinel lymph node/s is/are the target organs initially reached by metastasizing cancer cells from the tumour. The coated nanoparticles and composition comprising them can therefore be used for detection of sentinel lymph nodes and used as part of a sentinel node procedure comprising the identification, removal and analysis of the sentinel lymph nodes of a particular tumour.

In another application, the coated nanoparticles comprise a PSMA targeting group (e.g. antibody fragment or inhibitor) and the composition comprising them allows for detection of tissue overexpressing PSMA such as prostate cancer that have taken up the coated nanoparticles upon injection of the composition into a subject. That procedure can be used to identify tissue that is affected by prostate cancer. The coated nanoparticles and the composition comprising them can therefore be used for detection of prostate cancer in patients and can be used as part of focal therapy for ablating the prostate cancer cells, during surgery for assessing if all prostate cancer lesion is removed as part of a surgical procedure such as prostatectomy, and for detecting prostate cancer in lymph nodes for either surgical or radiotherapy planning.

EXAMPLES

Example 1: Preparation of an Iron Oxide Nanoparticle Solution in Water Using poly[(monoacryloyloxy)-ethyl]phosphonic acid-block-poly(acrylamide)

Part a) Preparation of Magnetic Particles in Organic Solution

Fe(oleate)$_3$ (3.6 g), oleic acid (0.64 mL) and octadecene (25 mL) were combined in a 3-necked round-bottom flask and stirred under vacuum at 120° C. for 2 hours. The reaction flask was opened to flowing nitrogen gas and heated to 320° C. After 1 hour the reaction was cooled to 150° C. and opened to air. The reaction was stirred in air at 120° C. for 18 hours. The solution was transferred to a 250 nL round bottom flask, Fe(oleate)$_3$ (14.0 g) and oleylamine (100 mL) were added to the reaction. The mixture was evacuated at 120° C. for 2 hours then opened to following nitrogen gas. The mixture was heated to 320° C. and held at temperature for 1 hour. The flask was cooled to 150° C. and opened to air. The mixture was stirred in air at 120° C. for 24 hours. The particles were diluted 1:1 with toluene and collected by centrifuge.

Part b) Synthesis of poly[(monoacryloyloxy)-ethyl]phosphonic acid-block-poly(acrylamide)

2-(((butylthio)carbonothioyl)-thio)-propanoic acid (0.5 g), acrylamide (10.4 g), 4,4'-azobis(4-cyanovaleric acid) (0.050 g), dioxane (20 g) and water (30 g) were combined, degassed with nitrogen gas. The mixture is heated to 70° C. for 3 hours. [2-(methacryloyloxy)-ethyl]phosphonic acid and 4,4'-azobis(4-cyanovaleric acid) were added to the reaction mixture and the mixture was degassed with nitrogen gas. The mixture was heated to 70° C. for 4 hours. The polymer was precipitated by adding the mixture to 200 mL of acetone. The solid is collected by filtration and washed 3 times with acetone. The crude polymer is purified by dissolving in water and precipitating with acetone followed by filtration and washing with acetone. The solid is dried in a vacuum oven at 40° C. for 24 hours.

Part c) Transfer and Stabilisation of the Iron Oxide Nanoparticles to Water

Particles were dispersed in tetrahydrofuran with ultrasonication and magnetically separated. The particles were dispersed in 1M hydrochloric acid with ultrasonication for 2 minutes. The particles were collected by magnetic separation washed with ethanol and acetone and dispersed in a 1:1 water:ethanol mixture. The polymer was dispersed in water and adjusted to pH 5 with sodium hydroxide. The solution was ultrasonicated for 1 minute then the pH was adjusted to 7.4 with sodium hydroxide. The solution was stirred overnight. The particles were collected by centrifuge and purified by dispersing in tetrahydrofuran and magnetically separating before washing with acetone and allowing to dry. The particles were suspended in water and aggregates were removed by centrifuge.

Example 2: Preparation of an Iron Oxide Nanoparticle Solution in Water Using poly[(monoacryloyloxy)-ethyl]phosphonic acid-block-poly(acrylamide)-mannose and poly[(monoacryloyloxy)-ethyl]phosphonic acid-block-poly(acrylamide)-block-(polyethylene glycol)

Part a) Maghemite Particles Synthesis Method

Magnetite particles were produced following the Massart method (Preparation of aqueous magnetic liquids in alkaline and acidic media. IEEE Transaction on Magnetics, 1981. MAG-17(2): p. 1247-1248). In a typical reaction, FeCl$_3$.6H$_2$O (0.432 g) was dissolved in hydrochloric acid (1 M, 0.8 mL). FeSO$_4$·7H$_2$O (0.232 g) was dissolved separately in hydrochloric acid (1M, 0.4 mL). The two solutions were mixed and diluted with 10 mL H$_2$O. The solution was stirred and 1.5 mL, of ammonia solution (28% w/w) was added slowly over 1 hour. The reaction changed colour from orange to black and a precipitate formed. Stirring was continued for a further 1 hour then the precipitate was allowed to settle and the liquid was decanted. The particles were washed twice with water. The particles were oxidised from magnetite to maghemite by dispersing in a solution of Fe(NO$_3$)$_3$·9H$_2$O (0.302 g) in nitric acid (1 M, 5.0 mL) and stirring while heating to 90° C. for 1 hour. The solution changed from black to orange/brown indicating the formation of maghemite. The particles were allowed to settle and the liquid was decanted. The particle solution was washed twice with water then dispersed with sonication in 5 mL of water.

Part b) Synthesis of poly[(monoacryloyloxy)-ethyl] phosphonic acid-block-poly(acrylamide)-block (polyethylene glycol)

A solution of acrylamide (7.3 g), 4,4'-azobis(4-cyanovaleric acid) (0.050 g), methoxy polyethylene glycol modified 2-{[butylsulfanyl)cabonothioyl]sulfanyl}propanoic acid (2.0 g), dioxane (15 g) and water (30 g) is prepared in a round bottom flask. The solution is stirred magnetically and purged with nitrogen gas for 15 minutes before heating to 70° C. for 3 hours. The mixture was allowed to cool then opened to air and [2-(methacryloyloxy)-ethyl]phosphonic acid (2.0 g) and 4,4'-azobis(4-cyanovaleric acid) (0.050 g) were added to the reaction mixture. The reaction was stirred magnetically and purged with nitrogen gas for 15 minutes before heating to 70° C. for 4 hours. The reaction mixture was cooled and the polymer was precipitated by slow addition of the mixture to 200 mL of acetone in a conical flask. The solid was collected by vacuum filtration and washed 3 times with acetone. The crude polymer was purified by dissolving in water and precipitating by slow addition into acetone. The purified polymer was collected by vacuum filtration and washed with acetone. The solid was dried in a vacuum oven at 40° C. for 24 hours.

Part c) Synthesis of poly[(monoacryloyloxy)-ethyl] phosphonic acid-block-poly(acrylamide)-mannose The polyacrylamide polymer (1.0 g) from example 1b is combined with amino phenyl mannose (0.050 g), MES hydrate (0.98 g) and water (40 mL) and stirred to dissolve. EDC.HCl (0.16 g) and NaOH (1M. 0.1 mL) are added and the reaction mixture is stirred for 20 hours. The polymer is purified using a centrifuge filter with a 3 kDa molecular weight cut off with the retained portion washed 3 times with 10 mL of water. The product is collected and freeze-dried.

Part d) Particle Stabilisation Using a Mixture of Polymers 2.0 g of poly[(monoacryloyloxy)-ethyl]phosphonic acid-block-poly(acrylamide)-block(polyethylene glycol) and 1.0 g of poly[(monoacryloyloxy)-ethyl]phosphonic acid-block-poly(acrylamide)-mannose are dissolved in 50 mL of water and sonicated. The pH is adjusted to 4 with NaOH (0.1 M). SPION suspension as per Massart method (5 wt % solids, 100 g) is added to the polymer solution. After 10 minutes the pH is adjusted to 5.5 with NaOH (0.1 M) and sonication was continued. After 30 minutes the pH is adjusted to 7.0 with NaOH (0.1 M). Sonication was continued for a total of 1 hour. The suspension is purified by dialysis and diluted with saline to give an isotonic solution at 20 mg Fe/mL.

Example 3: Iron-Core Particles Coated with PEGphos

Part a) Synthesis of Iron-Core Iron Oxide Shell Particles

[Fe(C$_5$H$_5$)(C$_6$H$_7$)] (0.6 g) is weighed into a glass sample vial and degassed with nitrogen. Oleylamine (3.0 mL) and paraffin (8.0 mL) are degassed with nitrogen and added to the vial. The mixture is stirred until fully dissolved. The solution is transferred to a glass pressure vessel under nitrogen. The glass pressure vessel is charged with 2 bar hydrogen gas and placed in an oven pre-heated to 110° C. After 40 hours, the temperature is increased to 130° C. at a rate of 0.1° C./min and held at this temperature for 24 hours. The bottle is removed from the oven, allowed to cool and opened to air. Toluene is added and the mixture is sonicated at 50° C. until dissolved. The mixture is purified by centrifuge at 4000 rpm for 20 minutes and the solid dispersed in 0.5:20 oleylamine:toluene.

Part b) Coating Particles with Methoxy-Poly(Ethylene Glycol)-Phosphate

The particle solution from part a) is purified by centrifuge at 4000 rpm for 20 minutes. The supernatant is removed and the pellet dried under a stream of air. The particles were dispersed in dichloromethane at 20 mg/mL separately the mPEG-phosphate (Mw=5000) is dispersed at 40 mg/mL in dichloromethane. Once dissolved the particle solution was added to the polymer solution and the sample was mixed in a vortex shaker for 20 minutes. An equal volume of tromethamine buffer (pH 9.0, 120 g/L) was added and the solution was transferred to a separating funnel. The same volume of hexane was added to the solution and the solution is mixed to transfer the particles to the aqueous layer. The same volume of tromethamine buffer (pH 8.0, 1.2 g/L) was added to the solution. The solution is mixed and allowed to separate. The aqueous layer was collected and washed twice with hexane. Residual hexane is removed by evaporation and the solution is purified with a 10 kDa Mw centrifuge filter and washed twice with tromethamine buffer (pH 8.0, 1.2 g/L). The final concentrate is dispersed with tromethamine buffer (pH 7.5, 0.6 g/L).

Example 4: Synthesis of Targeting Magnetic Particles Coated with a Fluorescent Tag

Part a) Synthesis of the Fluorescent Polymer

The polymer (0.5 g) from example 1b) is combined with ICG amine (0.076 g), MES hydrate (0.49 g) and water (20 mL) and stirred to dissolve. EDC·HCl (0.08 g) and NaOH (1M, 0.05 mL) are added and the reaction mixture is stirred for 20 hours. The polymer is purified using a centrifuge filter with a 3 kDa molecular weight cut off with the retained portion washed 3 times with 10 mL of water. The product is collected and freeze-dried.

Part b) Coating and Transfer of Magnetic Particles to Saline Solution

The PEG polymer (1.42 g), the mannose polyacrylamide polymer (1.0 g) and the polyacrylamide ICG polymer (0.72 g) are dissolved in 50 mL of water and sonicated. The pH is adjusted to 4 with NaOH (0.1 M). SPION suspension as per Massart method (5 wt % solids, 100 g) is added to the polymer solution. After 10 minutes the pH is adjusted to 5.5 with NaOH (0.1 M). After 30 minutes the pH is adjusted to 7.0 with NaOH (0.1 M). Sonication is continued for a total of 1 hour. The suspension is purified by dialysis and diluted with saline to give an isotonic solution.

Example 5: Synthesis of Magnetic Tracer with Varying Particle Sizes for Controlling the Rate of Uptake

Part a) Synthesis of Small Magnetic Particles

Maghenite particles were produced using a co-precipitation method. In a typical reaction, $FeCl_3 \cdot 6H_2O$ (0.22 g) was dissolved in water (6.0 mL) $FeSO_4 \cdot 7H_2O$ (0.12 g) was dissolved separately in water (6.0 mL). The two solutions were mixed and 20 μL of hydrochloric acid (37% w/w) was added. The solution was stirred and 0.75 mL of ammonia solution (28% w/w) was added rapidly. The solution was mixed using an ultrasonic probe at 20% power for 18 minutes. The solution was allowed to settle and the supernatant decanted. The precipitate was washed twice with water. The particles were oxidised from magnetite to maghemite by dispersing in a solution of $Fe(NO_3)_3 \cdot 9H_2O$ (0.850 g) in nitric acid (1 M, 6.0 mL) and stirred while heating to 90° C. for 1 hour. The particles were allowed to settle and the liquid was decanted. The particle solution was washed twice with water then dispersed with sonication in 4 mL of water. The particles were analysed by transmission electron microscopy and found to have an average diameter of 9.35±2.2 nm.

Part b) Particle Stabilisation with a Mixture of poly[(monoacryloyloxy)-ethyl]phosphonic acid-block-poly(acrylamide)-block(polyethylene glycol) and poly[(monoacryloyloxy)-ethyl]phosphonic acid-block-poly(acrylamide)-mannose 40.0 mg of poly[(monoacryloyloxy)-ethyl]phosphonic acid-block-poly(acrylamide)-block(polyethylene glycol) and 20.0 mg of poly[(monoacryloyloxy)-ethyl]phosphonic acid-block-poly(acrylamide)-mannose are dissolved in 1 mL of water and sonicated. The pH is adjusted to 4 with NaOH (0.1 M). SPION suspension as per example 5a was added to the polymer solution and ultra-sonicated for 10 minutes. The pH was adjusted to 6 with NaOH (0.1 M). After another 10 minutes of ultra-sonication the pH was adjusted to 7.0 with NaOH (0.1 M). Sonication was continued for a total of 30 minutes. The suspension was purified by centrifuge filtration and diluted with saline to give an isotonic solution at 20 mg Fe/mL. Analysis by transmission electron microscopy found the particles to have an average diameter of 20.0±5.2 nm. Analysis by dynamic light scattering gave a hydrodynamic diameter of 89.8 mu.

Part c) Combining the Two Sizes of Particles

The ultrasmall iron oxides particles from example 5b) were combined with iron oxide particles from example 2d). The two solutions were diluted to equal concentration and mixed at a 1:1 ratio. The resulting mixture was analysed by transmission electron microscopy and found to have a bimodal distribution with an average particle diameter of 13.26±6.7 nm. Analysis by dynamic light scattering gave a hydrodynamic diameter of 95.7 nm.

Example 6: Coating Magnetic Particles with poly[(monoacryloyloxy)-ethyl]phosphonic acid-block-poly(acrylamide)

Part a) Synthesis of Magnetic Particles $Fe(oleate)_3$ (2.8 g), oleylamine (3.1 mL) and docosane (10 mL) were combined in a 3-necked round-bottom flask and stirred under vacuum at 50° C. for 15 minutes. The reaction flask was opened to flowing nitrogen gas and heated to 320° C. After 1 hour the reaction was allowed to cool naturally to room temperature. Trimethylamine N-oxide (3 mg) was added to toluene (5 mL) together with 1 mL of the particle solution. The solution was stirred at 90° C. for 18 hours. The particles were collected by centrifuge then redispersed in 1:3 oleic acid:toluene (1 mL).

Part b) Preparation of the Particles for Coating

An acetate buffer solution (1 ml) pH 5.0 was added and the solution was stirred at 40° C. for 1 hour. The particles were collected by centrifuge and dispersed in 1 mL of toluene. An oxidising solution of tert-butanol (0.7 mL), polyvinylpyrrolidone (100 mcL of 40 wt % solution in water), potassium carbonate (50 mcL, of 5 wt % solution in water) and potassium permanganate/sodium periodate solution (0.4 mL). The oxidising solution is added to the toluene solution and stirred for 30 minutes. The solution is diluted with toluene (2 mL) and water (2 mL) and the organic layer is removed. The aqueous layer is washed with hexane then transferred to a centrifuge filter (50 kDa) and washed twice with water.

Part c) Transfer of Magnetic Particles to Water

Poly[(monoacryloyloxy)-ethyl]phosphonic acid-block-poly(acrylamide) from part 1b) was dissolved in water to give a 2 wt % solution. The pH was adjusted to 5.0 with sodium hydroxide. The nanoparticle solution from part b was diluted to 1 mL and added to the stirred polymer solution. The solution was stirred for 1 hour then adjusted to pH 7.0 with sodium hydroxide solution before stirring for 20 hours. The particles were purified by centrifuge filtration (50 kDa) and diluted with isotonic phosphate buffered saline and washed once more with phosphate buffered saline.

Example 7: Stability Testing of Tracers with Varying Polymers

The stability of three different tracers were tested by dispersing in water, phosphate buffered saline or saline and heating to 120° C. for 15 to 30 minutes. Two samples were tested with a single polymer which was either (i) mPEG-phosphonate as per example 3 or (ii) 5 phosphonate anchoring groups, with 45 polyethylene glycol monomer units. One sample (iii) was tested with a mixture of stabilising and targeting polymer as per example 2. Tracers (i) and (ii) showed aggregation with all of the nanoparticles precipitated to the bottom of the vessel and clear fluid above; tracer (iii) remained well dispersed with no visual signs of aggregation. Dynamic light scattering measurements on tracer (iii) showed no increase in the hydrodynamic diameter.

Example 8: Binding of Targeting Groups to Receptors

The binding of the targeting group on a variety of tracers to the mannose receptor was tested using a ConA dot blot assay. Particles were synthesised as per example 3 using stabilising polymers with 15 acrylamide monomer units and 3 polyethylene glycol units, 50 acrylamide units and 3 polyethylene glycol units and 50 acrylamide units and 16 polyethylene glycol units. The same targeting polymer with 70 acrylamide units was used in all cases. The particles were coated with the polymers with 30% targeting polymer and 70% stabilising polymer. The mannose receptor binding was tested in a ConA dot blot assay using the particle solution either in phosphate buffered saline or premixed with 10% serum. In the absence of serum the tracers all showed significant binding to the ConA protein. In the presence of serum the binding varied with the greatest binding observed when the length of the stabilising polymer was shortest and the least binding observed when the stabilising polymer was the longest.

Example 9: Animal Testing Using Tracer for Sentinel Lymph Node Identification

Part a) Testing Magnetic Nanoparticle Solution as an MRI Tracer for Sentinel Lymph Nodes in Swine The magnetic nanoparticle tracer solutions in saline were tested for use in sentinel lymph node identification by injection into Large White pigs. MRI scans were taken using a Siemens 3.0 T MRI. Five 0.2 mL injections of 20 mgFe/mL magnetic nanoparticle solution were injected into the tongue with one central injection and four quadrant injections distributed around the central site. Injections into the hind limbs 12 cm from the hoof were also performed in a similar five-injection pattern. Massage was performed on the injection sites for 5 minutes immediately after and 2 minutes every hour thereafter. MRI scans were repeated 30 minutes and 5 hours after injection. The sentinel lymph nodes were identified in both scans.

Part b) Uptake and Detection of Magnetic Tracer Solution into Sentinel Lymph Nodes in Swine The magnetic nanoparticles from were injected into the hind limb of a Large White pig. 0.5 ml, of the nanoparticle solution from part d) was injected in a quadrant 12 cm from the hoof, the injection site was massaged for 5 minutes immediately and 2 minutes every hour thereafter. MRI scans were taken using a Siemens 3.0 T MRI after 30 minutes. In a second animal the same injection was performed and scans were obtained after 30 minutes and 5 hours. The sentinel lymph nodes of both animals were excised and the uptake into the node was measured using a proprietary magnetic detector.

Part c) Uptake and Detection of Magnetic Tracer Solution into Sentinel Lymph Nodes in Rabbits and Clearance from the Injection Site The magnetic nanoparticles were tested for uptake into the lymph nodes and clearance from the injection site by testing with New Zealand White outbred rabbits. Five 0.1 mL injections of 6 mgFe/mL magnetic nanoparticle solution were injected into the tongue distributed around a central point. MRI scans of the animals were acquired prior to injection and prior to surgery. Surgery was performed after 2 or 24 hours to measure the uptake into the sentinel lymph nodes and clearance from the injection site using a proprietary magnetic detector.

Results

It was observed that the magnetic nanoparticles prepared according to the Examples and containing mannose in the coating composition (hereafter "mannose particles") outperformed Sienna+® (i.e. superparamagnetic iron oxide particles commercially available from Sysmex Europe GmbH) when corrected for dose (mg of Fe).

It was also observed that mannose particles do not flow on to 2nd echelon nodes but Sienna+® and particles without mannose do.

It was also observed that a higher concentration of tracer composition works better as larger volume results in reduced signal, and therefore particles stable at higher concentrations such as those described in this disclosure, are beneficial.

Comparison of Tracer Performance

In comparative tests, the following tracer compositions were assessed:

Sienna+® nanoparticles, and

Mannose particles prepared according to the present disclosure.

The tests were SLN uptake, 2nd echelon flow-through, and injection site signals on average for each site. The average also looked for general 'SLN vs. injection site' comparison. The results normalised to injected dose (mass of Fe).

Results

It was observed that the mannose particles do not flow on to lower echelon nodes.

Probe Signal in Nodes

The average signals for a range of sites were compared and all values were normalised to concentration (probe signal/total injected dose in mg Fe).

Results

Figure 13:
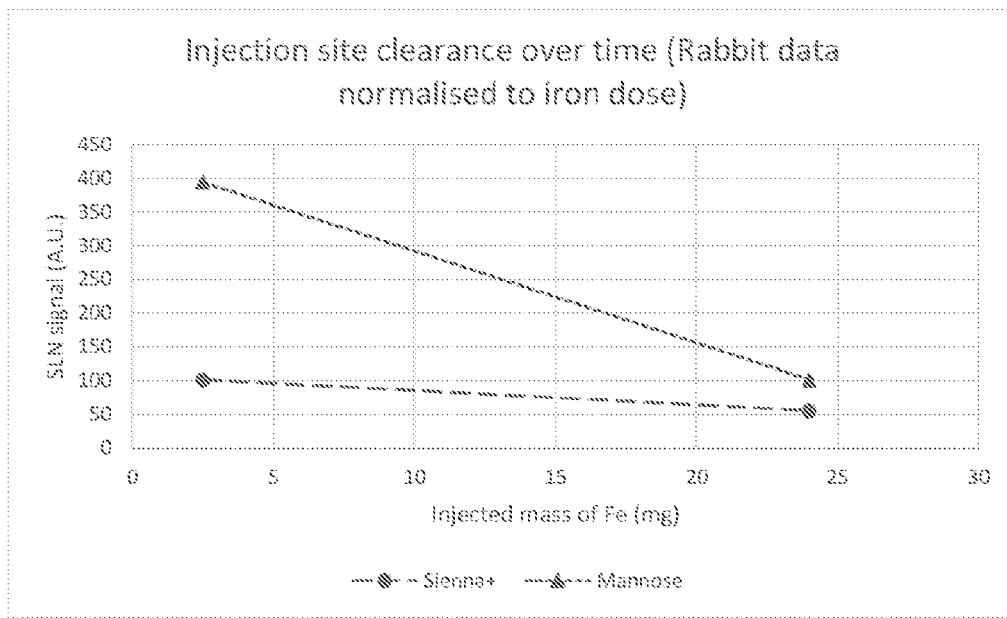
FIG. 13 shows a plot of injected mass of Fe vs magnetic signal from the injection site of rabbits after tongue injection of Sienna+® and mannose coated nanoparticles.

The results are shown in FIG. 13.

Probe Signal in Nodes—Average Signals

Figure 14:
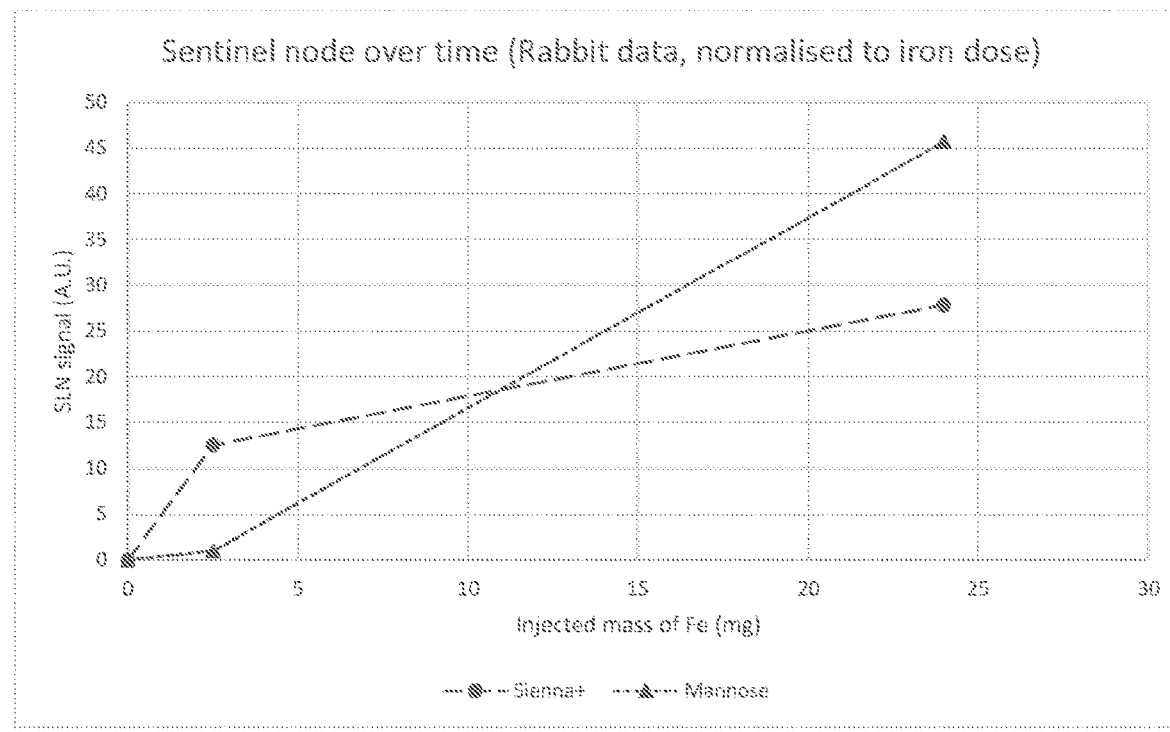
FIG. 14 shows a plot of injected mass of Fe vs magnetic signal from the injection site of rabbits after tongue injection of Sienna+® and mannose coated nanoparticles.

The data was then simplified to the average signals from the SLN and injection sites (two important metrics). The results are shown in FIG. 14.

On average, the SLN signal from mannose was best.

Clearance of Sienna+® and Mannose Particles

Clearance studies were performed over 2.5 to 24 hours in rabbits using Sienna+® and mannose particles.

Clearance studies were also performed over 1 to 6 hours in pigs using Sienna+® and mannose particles.

The probe signals of the injection site and nodes (normalised to injected Fe dose) were compared and the approximate rates of clearance/uptake over these time periods were observed.

Results

Sienna+® clears quickly to begin with but plateaus after a short time. Mannose particles clear at a steady rate into nodes.

Long-Term Clearance (Rabbit Data)

Figure 15:
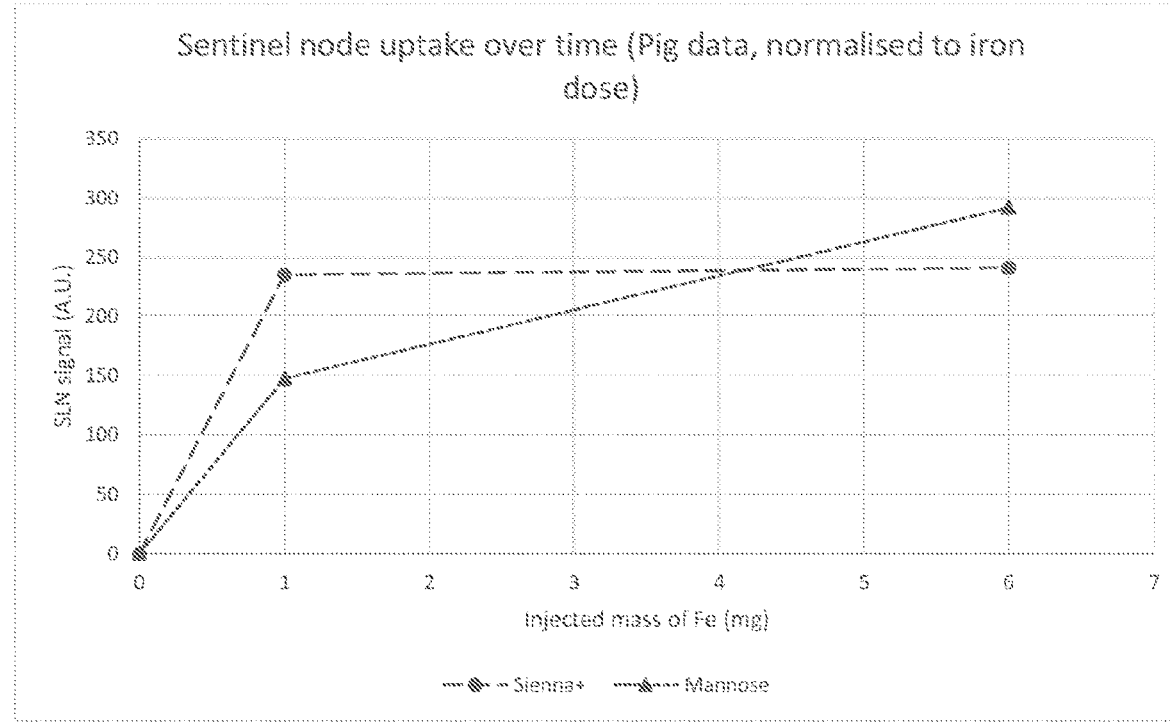
FIG. 15 shows a plot of injected mass of Fe vs magnetic signal from sentinel lymph nodes in the hind limb of swine for Sienna+® and mannose coated nanoparticles.

Tongue injection site signals from rabbits using Sienna+® and mannose particles were measured over time (FIG. 15).

Results

Sienna+® shows fast clearance in a short period of time (2.5 hours), and a slower rate of clearance over a 24 hour window (slope of line). Mannose particles have a steady clearance rate over 24 hours.

Long-Term SLN Uptake (Rabbit Data)

Figure 16:
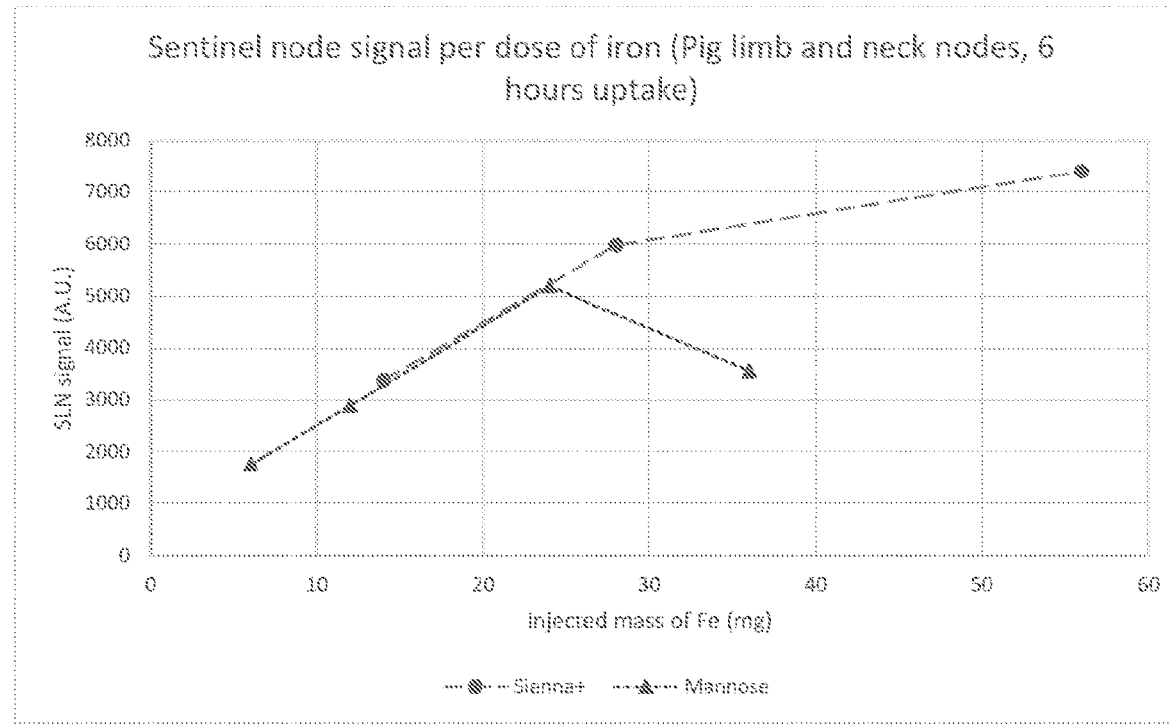
FIG. 16 shows a plot of injected mass of Fe vs magnetic signal for Sienna+® and mannose coated nanoparticles.

Head SLN signals from rabbits using Sienna+® and mannose particles were measured over time (FIG. 16).

Results

Sienna+® showed an initial rapid uptake (2.5 hours) but a slower slope over time. The mannose particles showed an increased slope indicating a faster uptake into the sentinel node per unit time.

Short-Term SLN Uptake (Pig Data)

Figure 17:
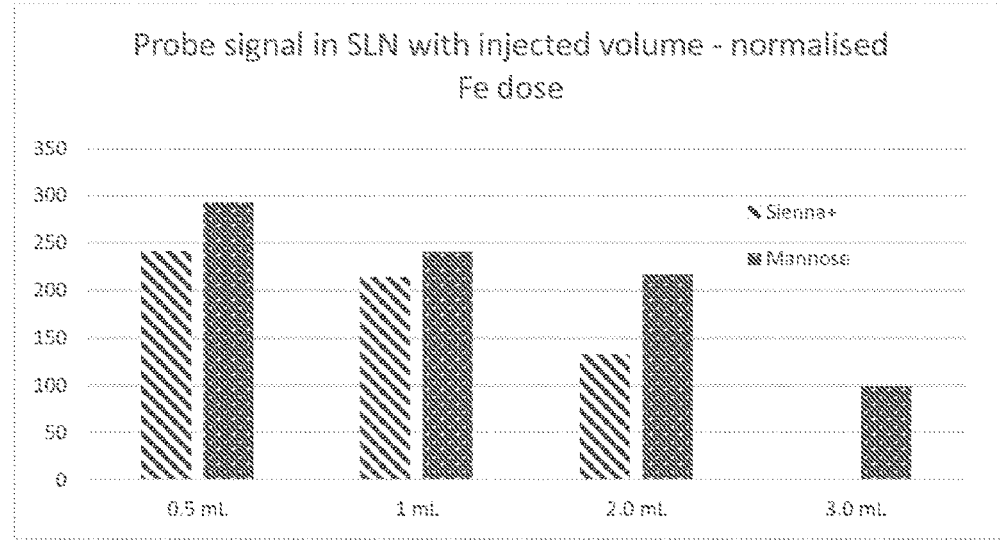
FIG. 17 shows a plot of the probe signal in SLN with injected volume normalised to Fe dose for Sienna+® and mannose coated nanoparticles.

The 1-6 hr uptake signals for 0.5 mL of Sienna+® and mannose particles in pig leg SLNs were compared (FIG. 17).

Results

Again, Sienna+® has faster initial uptake after injection, but plateaus quickly and shows little change after 2 hours.

Uptake of mannose particles consistently increases over time, indicating reliable clearance from the injection site.

Dosage for Sienna+ and Mannose

The outright probe signal was observed as the mass of iron content was changed (not normalised). The signal normalised to iron mass was also observed as the volume of tracer was increased.

Results

Increasing iron mass injected increased signal at a similar rate for both tracers. Increasing the volume of the injected dose decreased signal. A tracer stable at higher concentrations which therefore requires less volume is desirable.

Probe Signal with Mass of Fe

The outright probe signals (not normalised for Fe mass) for Sienna+® and mannose particles was observed as the injected dosage was changed (FIG. 18).

Results

Both Sienna+® and mannose particles were remarkably similar at lower doses (<30 mg). A 2 mL quantity (58 mg Sienna+® (vs. 24 mg mannose particles) gave the highest raw signal for each tracer. An observed drop off in signal for the highest dose (3 mL) may be due to tissue damage. Higher concentrations allowing lower volume injections are desirable, such as the concentrations enabled by the present disclosure.

Probe Signal with Dose Volume

The data was then normalised for the injected mass of Fe to see how SLN signal changes with volume (FIG. 19).

Results

Both Sienna+® and mannose particle SLN signals go down as the injected volume is increased. This effect was more evident in Sienna+®. Based on this data, a higher concentration, lower volume is preferred.

Example 10: Magnetic Nanoparticles with Polymer Composition Coating Comprising PSMA Polymeric Targeting Moiety Oleylamine coated Fe3O4 nanoparticles of 10 nm average core size are prepared via thermal decomposition of iron (III) acetylacetonate in organic solvents. Oleylamine coated particles dispersed in tetrahydrofuran (THF) are added drop wise to a polymer solution in THF, the polymer solution consisting of a 2:1 ratio of poly[(monoacryloyloxy)-ethyl] phosphonic acid-block(polyethylene glycol) (Mn 11, 000) and poly[(monoacryloyloxy)-ethyl]phosphonic acid-block (polyethylene glycol)-Glu-urea-Lys (Mn 11, 000) under probe sonication (1 min, 50% amplitude). A 10:1 ratio of polymer to nanoparticles is used. To achieve a complete exchange of the surface ligands the solution is heated to 50° C. and kept at this temperature for 24 h under magnetic stirring. Upon completion, the reaction is cooled down to room temperature and sample is precipitated using excess hexane and centrifugation (5 min, 3500 RPM). This step is repeated three times by resuspending the sample in the original volume of THF, hexane precipitation, centrifugation and removal of supernatant. Last, the sample is lightly dried using airflow and resuspended in MilliQ water. To remove any excess polymer sample is washed three times with MilliQ water using 100 kDa Amicon ultra centrifugal filters (5 min, 3500 RPM). For transfer into physiological buffers sample is mixed with 1.8% NaCl or 2×PBS in 1:1 volume ratio which yields stable nanoparticles colloidal solution in 0.9% NaCl or PBS.

The colloidal stability of the PSMA targeting group functionalized $Fe_3O_4$ nanoparticles in physiological buffers is measured using dynamic light scattering. Targeting ability to the PSMA targeting group is evaluated by studying the particles uptake in-vitro in human prostate adenocarcinoma cells (LNCaP cell line). Non-PSMA expressing cell line is used as a negative control. It was noted that the PSMA expressing cell line preferentially took up the PSMA targeting group functionalised nanoparticles.

The particles were then injected in the tail vein of both mice with orthotopic prostate tumours and mice with no tumours, using a dose of 4 mg/kg. After 24 hours, the mice were euthanized, and the prostates removed and studied by a veterinary pathologist. The prostates were stained using a Prussian blue stain to visualise the iron in the nanoparticles to determine if the PSMA targeted nanoparticles are preferentially bound to prostate tumour. It was noted the targeting group functionalised nanoparticles had been taken up on the boundary of the tumour, with some penetration along vessels. There was no staining evident with the control mice.

It will be appreciated by those skilled in the art that the disclosure is not restricted in its use to the particular application described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope of the disclosure as set forth and defined by the following claims.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

Please note that the following claims are provisional claims only, and are provided as examples of possible claims and are not intended to limit the scope of what may be claimed in any future patent applications based on the present application. Integers may be added to or omitted from the example claims at a later date so as to further define or re-define the invention.

What is claimed:

1. A pharmacologically acceptable magnetic nanoparticle suitable for administration to a subject, the magnetic nanoparticle having a polymer composition coating, the polymer composition comprising:
   (i) a polymeric steric stabilizer that promotes dispersion of the magnetic nanoparticle in a liquid, the polymeric steric stabilizer comprising (i) an anchoring polymer segment having one or more binding groups that bind the polymeric steric stabilizer to the magnetic nanoparticle, and (ii) a steric stabilizing polymer segment comprising a polyacrylamide-co-polyalkylene oxide block copolymer, wherein the anchoring polymer segment is different from the steric stabilizing polymer segment; and
   (ii) a polymeric targeting moiety, comprising (i) an anchoring polymer segment having one or more binding groups that bind the polymeric targeting moiety to the magnetic nanoparticle, (ii) a linking polymer segment consisting of polyacrylamide, wherein the anchoring polymer segment is different from the linking polymer segment, and (iii) one or more targeting groups, each targeting group independently being a monosaccharide group for selectively targeting monosaccharide receptors, or an antibody, an antibody fragment, or an inhibitor for selectively targeting Prostate Specific Membrane Antigen (PSMA);

wherein the linking polymer segment has at least 10 more polymerized monomer residue units than the stabilizing polymer segment.

2. The pharmacologically acceptable magnetic nanoparticle of claim 1, wherein the polyacrylamide-co-polyalkylene oxide block copolymer comprises about 8 to about 60 polymerized acrylamide units and about 2 to about 10 polymerized alkylene oxide units.

3. The pharmacologically acceptable magnetic nanoparticle of claim 1, wherein the linking polymer segment has less than about 100 polymerized acrylamide units.

4. The pharmacologically acceptable magnetic nanoparticle of claim 1, wherein the polymer composition further comprises (iii) a polymeric luminescent moiety comprising (i) an anchoring polymer segment having one or more binding group that bind the polymeric luminescent moiety to the magnetic nanoparticle, (ii) a linking polymer segment, wherein the anchoring polymer segment is different from the linking polymer segment, and (iii) one or more luminescent groups for emitting light or an acoustic signal in response to light that enables in vivo location visualisation of the magnetic nanoparticle.

5. The pharmacologically acceptable magnetic nanoparticle of claim 4, wherein the linking polymer segment of the polymeric luminescent moiety has (i) at least 10 more polymerized monomer residue units than the steric stabilizing polymer segment and (ii) less than about 100 polymerized monomer residue units.

6. The pharmacologically acceptable magnetic nanoparticle of claim 4, wherein the linking polymer segment of the polymeric luminescent moiety consists of polyacrylamide.

7. The pharmacologically acceptable magnetic nanoparticle of claim 1, wherein the polymer composition further comprises (iv) a luminescent group(s) that is not covalently coupled to a polymer.

8. The pharmacologically acceptable magnetic nanoparticle of claim 4, wherein each luminescent group is independently selected from the group consisting of indocyanine green, sulfo-Cy3, sulfo-Cy5, and sulfo-Cy7.

9. The pharmacologically acceptable magnetic nanoparticle of claim 1, wherein of the magnetic nanoparticle comprises iron (Fe), maghemite ($\gamma$-$Fe_2O_3$), magnetite ($Fe_3O_4$), or a combination thereof.

10. The pharmacologically acceptable magnetic nanoparticle of claim 1, wherein the one or more targeting group is mannose, glucose, or Lys-Urea-Glu.

11. The pharmacologically acceptable magnetic nanoparticle of claim 1, wherein the magnetic nanoparticle is a superparamagnetic nanoparticle.

12. A composition suitable for administration to a subject, comprising the pharmacologically acceptable magnetic nanoparticle of claim 1 and a pharmacologically acceptable liquid carrier.

13. A method for detecting a disease or disorder in a subject, the method comprising:
(i) administering the magnetic nanoparticle of claim 1 to the subject; and
(ii) detecting the magnetic nanoparticle in the subject,
wherein localization of the magnetic nanoparticle indicates the presence of the disease or disorder in the subject.

14. The method of claim 13, wherein the disease or disorder is cancer.

15. The method of claim 13, wherein the localization of the magnetic nanoparticle is to a sentinel lymph node of the subject.

16. A method for detecting cancer in a subject, the method comprising:
(i) administering the composition of claim 15 to the subject; and
(ii) detecting the magnetic nanoparticle in the subject,
wherein localization of the magnetic nanoparticle indicates the presence of tissue affected by cancer in the subject.

17. The pharmacologically acceptable magnetic nanoparticle of claim 1, wherein the anchoring polymer segment of the polymeric steric stabilizer, the anchoring polymer segment of the polymeric targeting moiety, or both comprises acrylic acid, methacrylic acid, itaconic acid, p-styrene carboxylic acids, p-styrene sulfonic acids, vinyl sulfonic acid, vinyl phosphonic acid, monoacryloxyethyl phosphate, 2-(methylacryloyloxy) ethyl phosphate, ethacrylic acid, alpha- chloroacrylic acid, crotonic acid, fumaric acid, citraconic acid, mesaconic acid, maleic acid, 2- (dimethyl amino) ethyl and propyl acrylates and methacrylates, the corresponding 3-(diethylamino) ethyl and propyl acrylates and methacrylates, [2-(methacryloyloxy)-ethyl]phosphonic acid and combinations thereof.

18. The pharmacologically acceptable magnetic nanoparticle of claim 1, wherein the anchoring polymer segment of the polymeric steric stabilizer, the anchoring polymer segment of the polymeric targeting moiety, or both comprises 1 to about 30 polymerized monomer residue units.

19. The pharmacologically acceptable magnetic nanoparticle of claim 1, wherein the anchoring polymer segment of the polymeric steric stabilizer, the anchoring polymer segment of the polymeric targeting moiety, or both comprises 1 to 10 phosphonate groups.

* * * * *